United States Patent
Barbic

(10) Patent No.: US 10,908,237 B2
(45) Date of Patent: Feb. 2, 2021

(54) MAGNETIC APPARATUS

(71) Applicant: Howard Hughes Medical Institute, Chevy Chase, MD (US)

(72) Inventor: Mladen Barbic, Sterling, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 15/945,512

(22) Filed: Apr. 4, 2018

(65) Prior Publication Data

US 2018/0292479 A1    Oct. 11, 2018

Related U.S. Application Data

(60) Provisional application No. 62/482,072, filed on Apr. 5, 2017, provisional application No. 62/632,201, filed on Feb. 19, 2018.

(51) Int. Cl.
  *G01R 33/31* (2006.01)
  *G01R 33/3815* (2006.01)
  (Continued)

(52) U.S. Cl.
  CPC .............. *G01R 33/31* (2013.01); *A61B 5/01* (2013.01); *A61B 5/055* (2013.01); *A61B 5/0515* (2013.01);
  (Continued)

(58) Field of Classification Search
  CPC .. G01R 33/31; G01R 33/281; G01R 33/5601; G01R 33/3815; A61B 5/01; A61B 5/0515; A61B 5/055; A61K 49/06; A61N 2/00
  See application file for complete search history.

(56) References Cited

U.S. PATENT DOCUMENTS 5,087,336 A * 2/1992 Liboff ...................... A61N 2/02
                                                                204/155
7,625,562 B2   12/2009 El Haj et al.
                       (Continued)

FOREIGN PATENT DOCUMENTS

| CN | 101601607 A | 12/2009 |
| CN | 105997944 A | 10/2016 |

(Continued)

OTHER PUBLICATIONS

Huang, "Remote control of ion channels and neurons through magnetic-field heating of nanoparticles", Nature Neuroscience, vol. 5 (Year: 2010).*

(Continued)

*Primary Examiner* — Joanne M Hoffman
(74) *Attorney, Agent, or Firm* — DiBerardino McGovern IP Group LLC

(57) ABSTRACT

An apparatus includes a magnetic apparatus that defines an actuation volume that is large enough to accommodate a sample, the magnetic apparatus including a magnet that is configured to create a magnetic field having a magnitude B in the sample when supplied with a DC current; at least one biological construct within the sample, the biological construct configured to change its status in response to a change in a property; and at least one magnetocaloric actuator coupled with the biological construct. A change in a characteristic in the actuation volume causes the property of the magnetocaloric actuator to change, which causes a change in the status of the biological construct.

38 Claims, 18 Drawing Sheets

(51) Int. Cl.
| | |
|---|---|
| *A61K 49/06* | (2006.01) |
| *A61B 5/055* | (2006.01) |
| *G01R 33/56* | (2006.01) |
| *A61N 2/00* | (2006.01) |
| *A61B 5/05* | (2006.01) |
| *A61B 5/01* | (2006.01) |
| *G01R 33/28* | (2006.01) |

(52) U.S. Cl.
CPC ............... *A61K 49/06* (2013.01); *A61N 2/00* (2013.01); *G01R 33/281* (2013.01); *G01R 33/3815* (2013.01); *G01R 33/5601* (2013.01)

(56) References Cited

U.S. PATENT DOCUMENTS

| | | | | |
|---|---|---|---|---|
| 2004/0023203 | A1 | 2/2004 | Miesenbock et al. | |
| 2005/0025797 | A1* | 2/2005 | Wang | A61L 31/16 424/422 |
| 2005/0149169 | A1* | 7/2005 | Wang | A61F 2/82 623/1.15 |
| 2005/0249817 | A1* | 11/2005 | Haik | A61K 33/24 424/617 |
| 2006/0008924 | A1* | 1/2006 | Anker | G01N 33/58 436/526 |
| 2008/0078476 | A1* | 4/2008 | Saito | B22F 9/10 148/328 |
| 2010/0259259 | A1* | 10/2010 | Zahn | G01R 33/5601 324/309 |
| 2011/0270360 | A1* | 11/2011 | Harris | A61N 1/36 607/62 |
| 2013/0309702 | A1* | 11/2013 | Kim | A61K 49/1866 435/18 |
| 2018/0200386 | A1* | 7/2018 | Stanley | A61K 48/00 |

FOREIGN PATENT DOCUMENTS

| | | |
|---|---|---|
| WO | 2010052471 A1 | 5/2010 |
| WO | 2016205291 A1 | 12/2016 |

OTHER PUBLICATIONS

Huang, "Remote control of ion channels and neurons through magnetic-field heating of nanoparticles", Nature Neuroscience, vol. 5, supplemental (Year: 2010).*
Duret, "Magnetic entropy as a gating mechanism for magnetogenetic ion channels" (Year: 2017).*
Wheeler, "Genetically targeted magnetic control of the nervous system", Nature Neuroscience, vol. 16 (Year: 2016).*
Wheeler, "Genetically targeted magnetic control of the nervous system", Nature Neuroscience, vol. 16, supplemental (Year: 2016).*
Stanley, "Radio-Wave Heating of Iron Oxide Nanoparticles Can Regulate Plasma Glucose in Mice", Science, vol. 336 (Year: 2016).*
Sruthi Polali, "Novel Mechanisms for Magnetogenetic neuromodulation" (Year: 2013).*
Eric T. Ahrens et al., "Tracking immune cells in vivo using magnetic resonance imaging," Nature Reviews, Immunology, Oct. 2013, vol. 13, https://www.nature.com/reviews/immunol, pp. 755-763 (9 total pages).
Erik M. Shapiro et al., "MRI detection of single particles for cellular imaging," PNAS, Jul. 27, 2004, vol. 101, No. 30, http://www.pnas.org/cgi/doi/10.1073/pnas.0403918101, pp. 10901-10906 (6 total pages).
Gary Zabow et al., "Micro-engineered local field control for high-sensitivity multispectral MRI," Nature, vol. 453, Jun. 19, 2008, doi: 10.1038/nature07048, pp. 1058-1063 (7 total pages).
Gary Zabow et al., "Shape-changing magnetic assemblies as high-sensitivity NMR-readable nanoprobes," Nature, vol. 520, Apr. 2, 2015, doi: 10.1038/nature14294, pp. 73-87 (15 total pages).

V. Franco et al., "The Magnetocaloric Effect and Magnetic Refrigeration Near Room Temperature: Materials and Models," Annual Reviews Mater Res., May 29, 2012, doi: 10.1146/annurev-matsci-062910-100356, https://www.annualreviews.org/, pp. 305-342 (40 total pages).
J.S. Kouvel et al., "Anomalous Magnetic Moments and Transformations in Ordered Alloy FeRh," Journal of Applied Physics, Supplement to vol. 33, No. 3, Mar. 1962, pp. 1343-1344 (2 total pages).
X. Marti et al., "Room-temperature antiferromagnetic memory resistor," Nature Materials, vol. 13, Jan. 26, 2014, https://www.nature.com/naturematerials, doi: 10.1038/nmat3861, pp. 367-374 (8 total pages).
J.B. Mckinnon et al., "The Antiferromagnetic-Ferromagnetic Transition in Iron-Rhodium Alloys," J. Phys. C: Metal Phys. Suppl., No. 1, 1970, pp. S46-S58 (13 total pages).
Jian Liu et al., "Giant magnetocaloric effect driven by structural transitions," Nature Materials, vol. 11, May 27, 2012, https://www.nature.com/naturematerials, doi: 10.1038/nmat3334, pp. 620-626 (7 total pages).
Enke Liu et al., "Stable magnetostructural coupling with tunable magnetoresponsive effects in hexagonal ferromagnets," Nature Communications, 3:873, https://www.nature.com/naturecommunications, doi: 10.1038/ncomms1868, 2012, pp. 1-10 (10 total pages).
Ritchie Chen et al., "Wireless magnetothermal deep brain stimulation," Mar. 27, 2015, Science, vol. 347, Issue 6229, pp. 1477-1480 (5 total pages), http://science.sciencemag.org/.
G.V. Brown, "Magnetic heat pumping near room temperature," Journal of Applied Physics, vol. 47, Issue 8, Aug. 1976, pp. 3673-3680 (8 total pages).
Jan-Ulrich Thiele et al., "FeRh/FePt exchange spring films for thermally assisted magnetic recording media," Applied Physics Letters, Apr. 28, 2003, vol. 82, No. 17, pp. 2859-2861 (4 total pages).
J.S. Kouvel, "Unusual Nature of Abrupt Magnetic Transition in Ferh and Its Pseudobinary Variants," Journal of Applied Physics, vol. 37, Issue 3, Mar. 1, 1966, pp. 1257-1258 (2 total pages).
V.I. Zverev et al., "The maximum possible magnetocaloric Δt effect," Journal of Applied Physics 107, 2010, https://doi.org/10.1063/1.3309769, pp. 043907-1-043907-3 (3 total pages).
M.P. Annaorazov et al., "Alloys of the Fe—Rh System as a New Class of Working Material for Magnetic Refrigerators," Cryogenics, 1992, vol. 32, No. 10, pp. 867-872 (6 total pages).
S.A. Nikitin et al., "The magnetocaloric effect in Fe49Rh51 compound," Applied Physics Letters, Aug. 27, 1990, vol. 148, No. 6,7, pp. 363-366 (4 total pages).
Heng Huang et al., "Remote control of ion channels and neurons through magnetic-field heating of nanoparticles," Nature Nanotechnology, vol. 5, https://www.nature.com/naturenanotechnology, doi: 10.1038/nnano2010.125, Jun. 27, 2010, pp. 602-606 (5 total pages).
Joris Vriens et al., "Peripheral thermosensation in mammals," Nature Reviews, Neuroscience, vol. 15, Sep. 2014, https://www.nature.com/reviews/neuro, pp. 579-589 (17 total pages).
Ardem Patapoutian et al., "Thermotrp Channels and Beyond: Mechanisms of Temperature Sensation," Nature Reviews, Neuroscience, vol. 4, Jul. 2003, https://www.nature.com/reviews/neuro, pp. 529-539 (11 total pages).
David E. Clapham et al., "The TRP Ion Channel Family," Nature Reviews, Neuroscience, vol. 2, Jun. 2001, https://www.nature.com/reviews/neuro, pp. 387-396 (10 total pages).
David E. Clapham et al., "TRP Channels as cellular sensors," Nature, vol. 426, Dec. 4, 2003, www.nature.com/nature, pp. 517-524 (8 total pages).
S. Yu. Dan'kov et al., "Magnetic phase transitions and the magnetothermal properties of gadolinium," Physical Review B, Vo. 57, No. 6, Feb. 1, 1998, pp. 3478-3490 (13 total pages).
Michael J. Rust et al., "Sub-diffraction-limit imaging by stochastic optical reconstruction microscopy (STORM)," Nat Methods, Oct. 2006, 3(10): 793-795, doi: 10.1038/nmeth929, pp. 1-7 (7 total pages).
Samuel T. Hess et al., "Ultra-high resolution imaging by fluorescence photoactivation localization microscopy," Biophysical Journal, vol. 91, Dec. 2006, pp. 4258-4272 (15 total pages).

(56) References Cited

OTHER PUBLICATIONS

Eric Betzig et al. "Imaging intracellular fluorescent proteins at nanometer resolution," Science, vol. 313, Sep. 15, 2006, http://science.sciencemag.org/, pp. 1642-1645 (5 total pages).

G.C. Han et al., "Magnetic stability of ultrathin FeRh films," Journal of Applied Physics 113, Mar. 2013, pp. 17C107-1-17C107-3 (3 total pages).

Ryoko Ando et al., "An optical marker based on the UV-induced green-to-red photoconversion of a fluorescent protein," PNAS, vol. 99, No. 20, Oct. 1, 2002, doi: 10.1073/pnas.202320599, pp. 12651-12656 (6 total pages).

C. Baldasseroni et al., "Temperature-driven nucleation of ferromagnetic domains in FeRh thin films," Applied Physics Letters 100, 2012, https://doi.org/10.1063/1.4730957, pp. 262401-1-262401-5 (5 total pages).

Ippei Suzuki et al., "Stability of ferromagnetic state of epitaxially grown ordered FeRh thin films," Journal of Applied Physics 105, 2009, https://doi.org/10.1063/13054386, pp. 07E501-1-07E501-3 (3 total pages).

C. Marquina et al., "Magnetic and magnetoelastic behavior of mechanically alloyed FeRh compound," Journal of Applied Physics 81, Mar. 1, 1997, doi: 10.1063/1364290, pp. 2315-2320 (6 total pages).

Seda Aksoy et al., Tailoring magnetic and magnetocaloric properties of martensitic transitions in ferromagnetic Heusler alloys, Applied Physics Letters 91, 2007, https://doi.org/10.1063/1.2825283, pp. 241916-1-241916-3 (3 total pages).

Radhika Barua et al., "Towards tailoring the magnetocaloric response in FeRh-based ternary compounds," Journal of Applied Physics 115, 2014, doi: 10.1063/1A854975, pp. 17A903-1-17A903-3 (3 total pages).

R. Kainuma et al., "Magnetic-field-induced shape recovery by reverse phase transformation," Nature, vol. 439, Feb. 23, 2006, doi: 10.1038/nature04493, pp. 957-960 (4 total pages).

W. Ito et al., "Atomic ordering and magnetic properties in the Ni45Co5Mn36.71n13.3 metamagnetic shape memory alloy," Applied Physics Letters 93, 2008, doi: 10.1063/1.3043456, pp. 232503-1-232503-3 (3 total pages).

Daniel Bourgault et al., "Large inverse magnetocaloric effect in Ni45Co5Mn37.5In12.5 single crystal above 300 K," Applied Physics Letters 96, 2010; doi: 10.1063/1.3372633, pp. 132501-1-132501-3 (3 total pages).

M. Pasquale et al., "Magnetostructural transition and magnetocaloric effect in Ni55Mn20Ga25 single crystals," Physical Review B 72, 2005, https://doi.org/10.1103/PhysRevB.72.094435, pp. 094435-1-094435-5 (5 total pages).

Yeonkyung Kim, Korean International Searching Authority, International Search Report and Written Opinion, counterpart PCT Application No. PCT/US2018/026096, dated Jul. 19, 2018 (12 total pages).

O. Tegus et al., "Transition-metal-based magnetic refrigerants for room-temperature applications," Nature, vol. 415, Jan. 10, 2002, www.nature.com, pp. 150-152 (3 total pages).

H. Wada et al., "Giant magnetocaloric effect of MnAs1-xSbx," Applied Physics Letters, vol. 79, No. 20, https://doi.org/10.1063/1.1419048, Nov. 12, 2001, pp. 3302-3304 (3 total pages).

Thorsten Krenke et al., "Inverse magnetocaloric effect in ferromagnetic Ni—Mn—Sn alloys," Nature Materials, vol. 4, Jun. 2005, https://www.nature.com/naturematerials, pp. 450-454 (5 total pages).

Katsuhiko Nishimura et al., "Magnetocaloric effect of Fe(Rh1-xPdx) alloys," Materials Transactions, vol. 49, No. 8, 2008, doi: 10.2320/matertrans.MRA2008080, pp. 1753-1756 (4 total pages).

Z. Jia et al., "Synthesis and magnetic properties of self-assembled FeRh nanoparticles," Applied Physics Letters 93, 2008, https://doi.org/10.1063/1.2952956, pp. 022504-1-022504-3 (3 total pages).

Hnin Yu Yu Ko et al., "Magnetic and structural characterizations on nanoparticles of FePt, FeRh and their composites," Journal of Magnetism and Magnetic Materials 320, Aug. 22, 2008, https://www.elseviercom/locate/jmmm, pp. 3120-3123 (4 total pages).

J. M. Lommel, "Magnetic and Electrical Properties of FeRh Thin Films," Journal of Applied Physics, vol. 37, No. 3, Mar. 1, 1966, https://doi.org/10.1063/1.1708527, pp. 1483-1484 (2 total pages).

J. M. Lommel et al., "Effects of Mechanical and Thermal Treatment on Structure and Magnetic Transitions in FeRh," Journal of Applied Physics, vol. 38, No. 3, Mar. 1, 1967, https://doi.org/10.1063/1.1709570, pp. 1263-1264 (2 total pages).

Tiejun Zhou et al., "On the origin of giant magnetocaloric effect and thermal hysteresis in multifunctional alpha-FeRh thin films," Physics Letters A 377, www.elsevier.com/locate/pla, 2013, pp. 3052-3059 (8 total pages).

X. Moya et al., "Caloric materials near ferroic phase transitions," Nature Materials, vol. 13, May 2014, https://www.nature.com/naturematerials, doi: 10.1038/nmat3951, pp. 439-450 (12 total pages).

Makoto Takahashi et al., "Annealing Effect on Phase-Transition of Equiatomic Ferh Alloy," Materials Transactions, JIM, vol. 36, No. 6, 1995, doi: 10.2320/matertrans1989.36.735, pp. 735-742 (8 total pages).

J.H. Hankiewicz et al., "Ferromagnetic particles as magnetic resonance imaging temperature sensors," Nature Comm'ns, vol. 7 (2016), doi: 10.1038/ncomms12415.

Arnaud Hillion et al., "Low Temperature Ferromagnetism in Chemically Ordered FeRh Nanocrystals," Physical Review Letters, vol. 110, No. 8 (2013), doi: 10.1103/PhysRevLett.110.087207, HAL Id: hal-02175801.

V. Uhlíř et al., "Colossal magnetic phase transition asymmetry in mesoscale FeRh stripes," Nature Comm'ns, vol. 7 (2016), doi: 10.1038/ncomms13113.

"Magnetocaloric Materials Calorivac: Advanced Materials—the Key to Progress," PCV-001 Edition, Vacuumschmelze GmbH & Co. Kg (2015).

Examiner Nicolas Vanhaecke, Extended European Search Report, European Patent Office, Counterpart Application No. 18780541.1, dated Dec. 14, 2020 (12 pages total).

\* cited by examiner

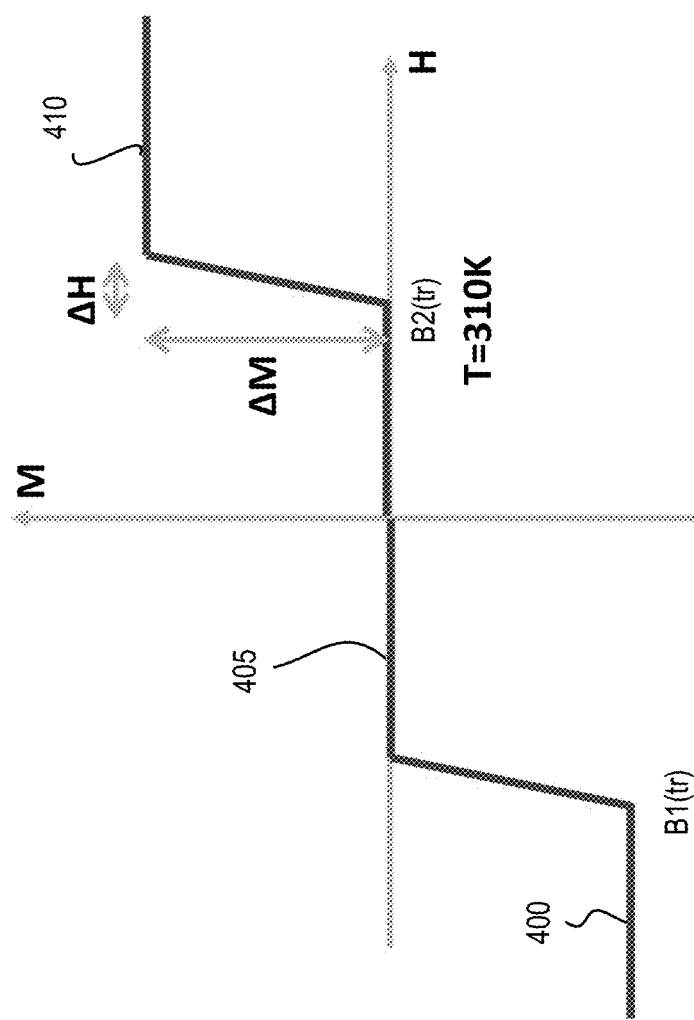
Fig. 4
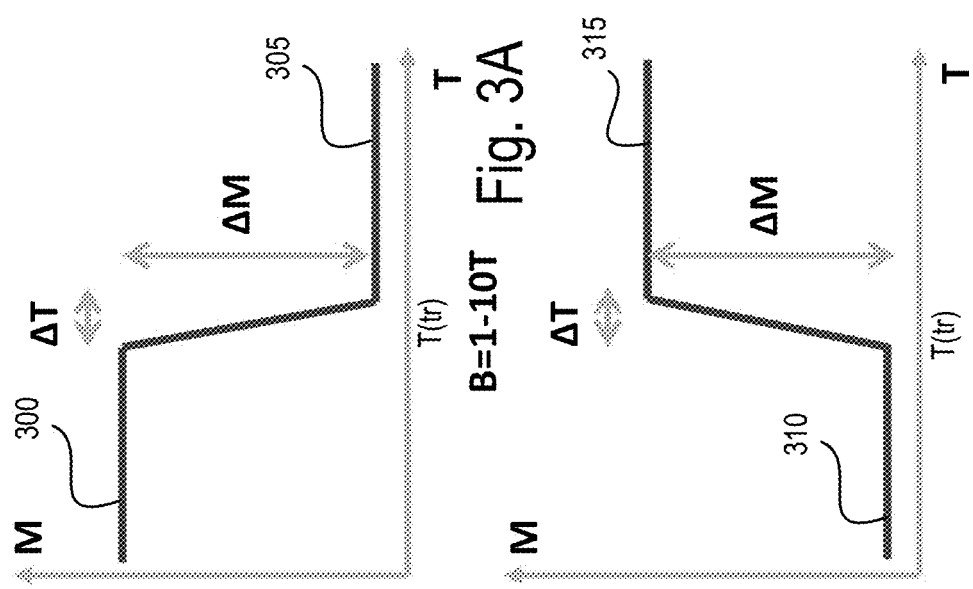
Fig. 3A
Fig. 3B

T=250-350K at constant magnetic field

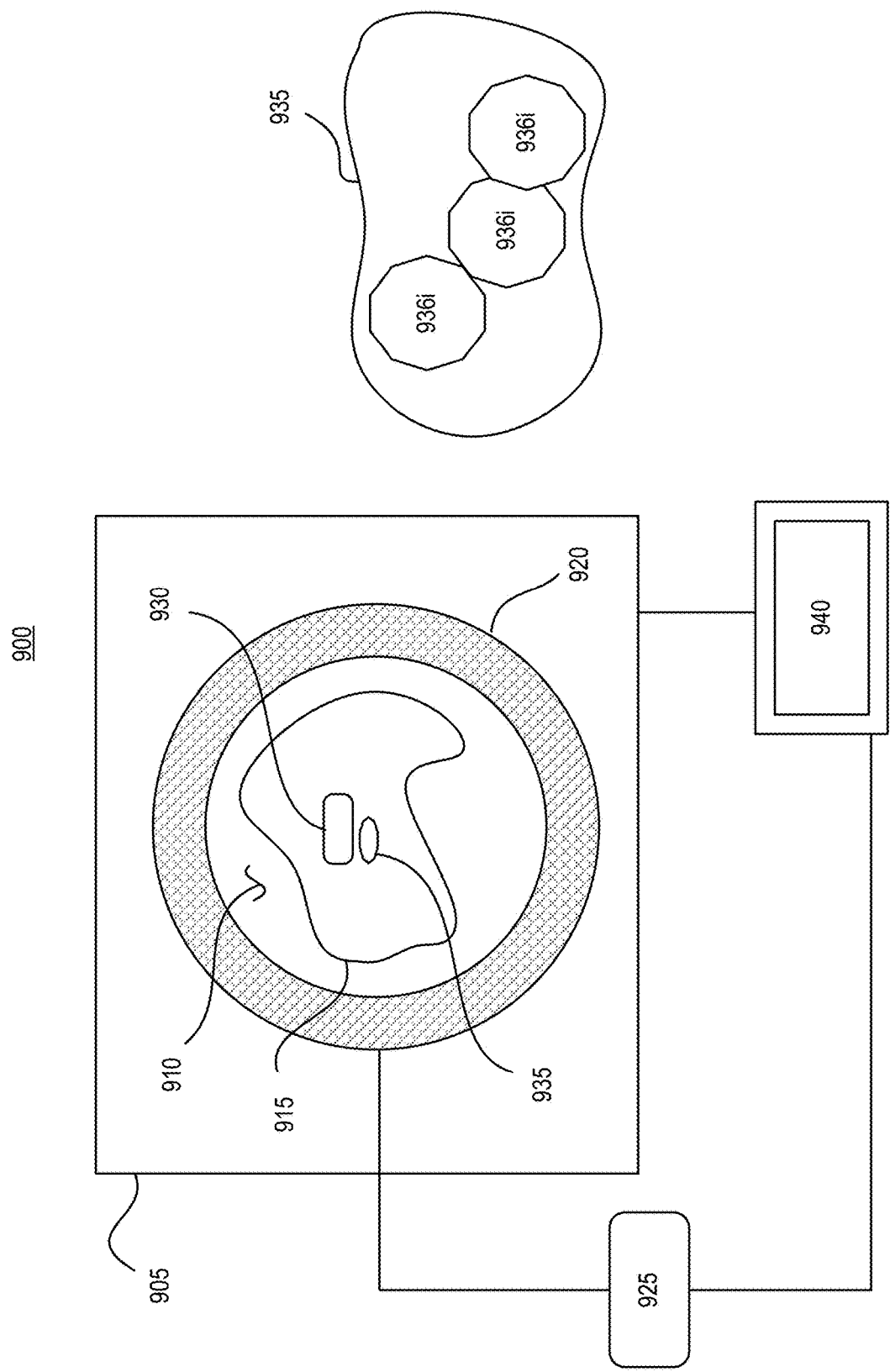

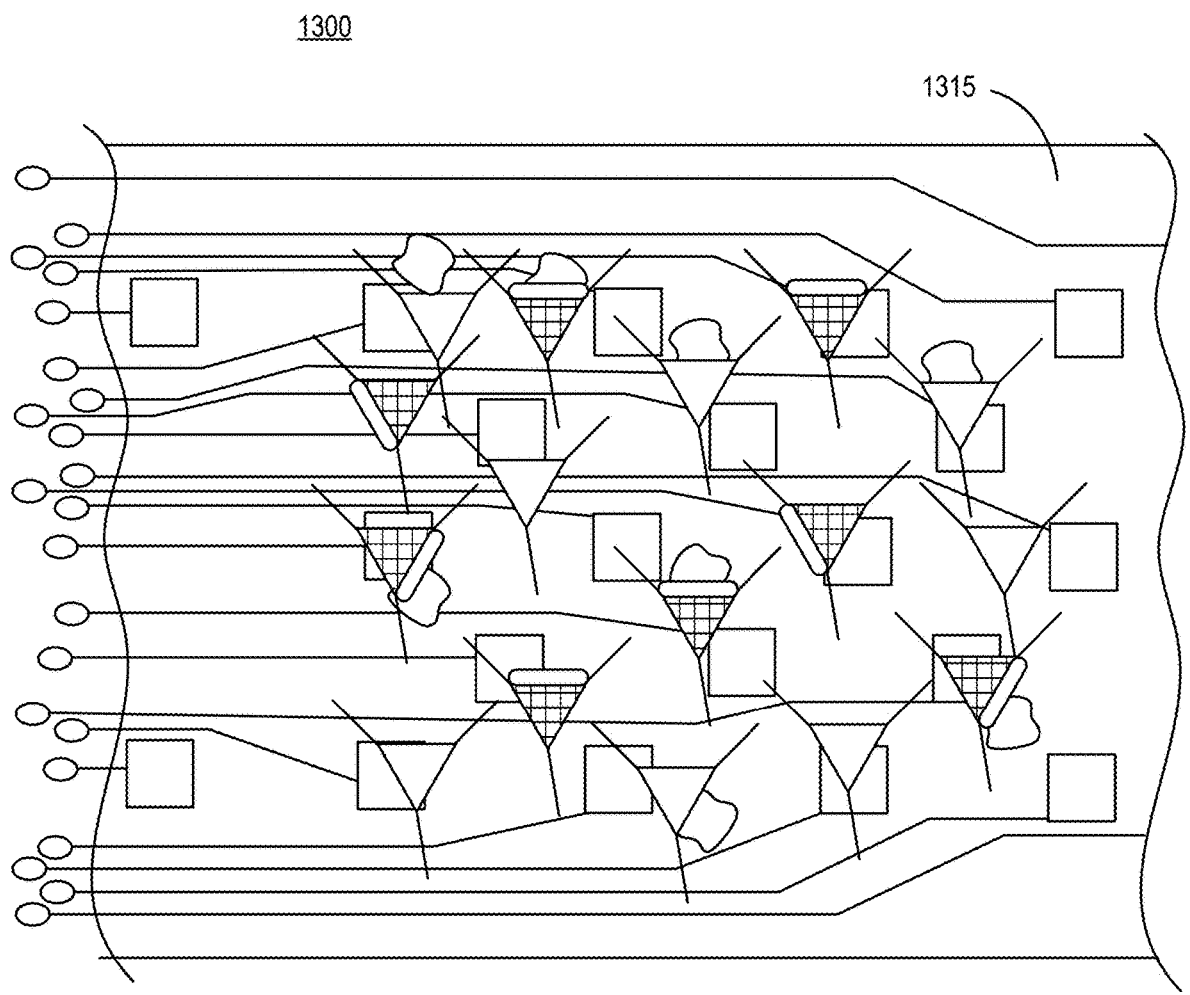
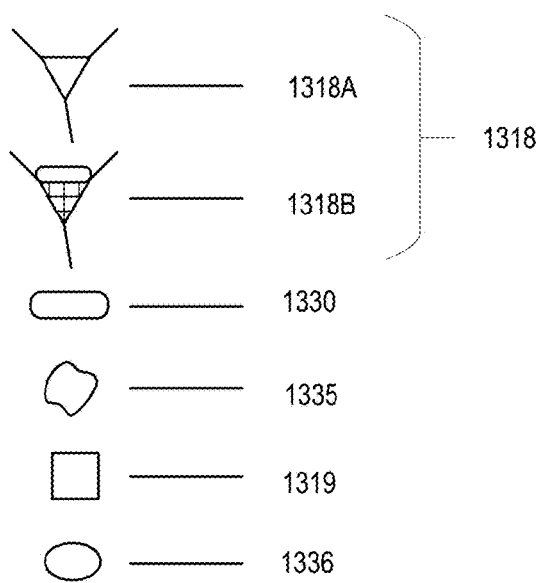
Fig. 13

MAGNETIC APPARATUS

CROSS REFERENCE TO RELATED APPLICATIONS

This application claims priority to U.S. Provisional Application No. 62/482,072, filed Apr. 5, 2017 and to U.S. Provisional Application No. 62/632,201, filed Feb. 19, 2018, both of which are incorporated herein by reference in their entirety.

TECHNICAL FIELD

The disclosed subject matter relates to magnetic apparatuses that employ magnetically manipulatable materials within a sample.

BACKGROUND

Magnetic apparatuses can be used for imaging. For example, a magnetic imaging apparatus such as a magnetic resonance imaging (MM) apparatus uses magnetic fields to image or visualize internal structures of samples such as a physiological or biological sample. An MRI apparatus can use labels in the sample to help imaging.

SUMMARY

In some general aspects, an apparatus includes: a magnetic apparatus that defines an actuation volume that is large enough to accommodate a sample; at least one biological construct within the sample, and at least one magnetocaloric actuator coupled with the biological construct. The magnetic apparatus includes a magnet that is configured to create a magnetic field having a magnitude B in the sample when supplied with a DC current. The biological construct is configured to change its status in response to a change in a property. A change in a characteristic in the actuation volume causes the property of the magnetocaloric actuator to change, which causes a change in the status of the biological construct.

Implementations can include one or more of the following features. For example, the sample can be a region of a live human body and the magnetocaloric property can change while the temperature in the live human body region is at a human body temperature.

The change caused to the property of the magnetocaloric actuator can occur without causing a change in status of materials within the sample other than the at least one biological construct.

The apparatus can include an energy supply connected to the magnet, and the magnet can include electrically conductive wire coils through which current from the energy supply is passed. The energy supply can provide the DC current supplied to the wire coils.

The magnet can be a superconducting magnet.

The magnetic field magnitude B can be greater than 0.5 Tesla or in a range of 1-20 Tesla.

The magnetic apparatus can be a magnetic resonance imaging apparatus.

The magnetocaloric actuator can include a material selected from the group consisting of iron-rhodium, alloys of iron-rhodium, alloys of manganese arsenide, Heusler alloys, alloys of manganese-iron, and gadolinium.

The sample can be a living organism and the sample can be held at a physiological temperature to maintain the organism in a living state.

Each magnetocaloric actuator can be a spatially-separated particle having a size on the order of about 1-100 μm.

The biological construct can be a thermally-sensitive biological construct; the at least one magnetocaloric actuator can be thermally coupled with the thermally-sensitive biological construct; and a change in the magnitude B of the magnetic field supplied with DC current can cause the temperature of the magnetocaloric actuator to change, which causes a change in the status of the thermally-sensitive biological construct. The magnetocaloric actuator can be a magnetically manipulatable material that exhibits a transition between a first magnetic state and a second magnetic state in response to the change in the magnitude B of the magnetic field. The change in the magnitude of the magnetic field can be substantially smaller than the magnitude B of the magnetic field.

The magnetically manipulatable material can exhibit the transition while the temperature in the sample is between 270 and 370 K.

The at least one thermally-sensitive biological construct within the sample can include an ion channel, and the ion channel can have a status that is either closed or open. The ion channel can be genetically-engineered. The ion channel can be a transient receptor potential cation channel subfamily V member. The ion channel can be a transient receptor potential cation channel subfamily M member.

An increase in the magnitude B of the magnetic field supplied with the DC current can cause an increase in the temperature of the magnetocaloric actuator and an increase in the temperature of the thermally-sensitive biological construct; and a decrease in the magnitude B of the magnetic field supplied with the DC current can cause a decrease in the temperature of the magnetocaloric actuator and a decrease in the temperature of the thermally-sensitive biological construct.

An increase in the magnitude B of the magnetic field supplied with the DC current can cause a decrease in the temperature of the magnetocaloric actuator and a decrease in the temperature of the thermally-sensitive biological construct; and a decrease in the magnitude B of the magnetic field supplied with the DC current can cause an increase in the temperature of the magnetocaloric actuator and an increase in the temperature of the thermally-sensitive biological construct.

Each magnetocaloric actuator thermally coupled with a first thermally-sensitive biological construct can be distinct from each magnetocaloric actuator thermally coupled with a second thermally-sensitive biological construct.

Each magnetocaloric actuator can be a spatially-separated particle having a size that is large enough to retain heat long enough to cause the change in status in the adjacent thermally-sensitive biological construct.

The magnetocaloric actuator temperature change $\Delta T$ can be less than 20° C. for a change in magnitude of the magnetic field $\Delta B$ between 1-20 T.

In other general aspects, a method includes: receiving a sample in a sample volume defined by a magnetic apparatus; physically coupling at least one magnetocaloric actuator within the sample with a biological construct within the sample such that the biological construct changes its status in response to a change in a property of the magnetocaloric actuator; creating a magnetic field having a magnitude B in the sample; and changing a characteristic associated with the sample by changing an operating property of the magnetic apparatus. Changing the sample characteristic causes the property of the magnetocaloric actuator to change, which causes a change in a status of the biological construct.

Implementations can include one or more of the following features. For example, creating the magnetic field having magnitude B can include creating a magnetic field having a magnitude B that is at least 0.5 Tesla and changing the operating property of the magnetic apparatus can include changing the magnitude of the magnetic field by an amount that is in a range of 1-20 Tesla.

The temperature of an environment of the sample can be maintained at a value between 270 and 370 K.

The operating property of the magnetic apparatus can be changed by changing the magnitude B of the magnetic field B by an amount that is substantially smaller than the magnitude B.

The sample can be a living organism, and the method can also include maintaining a temperature of the sample at a physiological temperature to maintain the organism in a living state. The sample can be a living organism, and the method can also include maintaining the sample environment at a physiological temperature to maintain the organism in a living state.

The magnetocaloric actuator can include a material selected from the group consisting of iron-rhodium, alloys of iron-rhodium, alloys of manganese arsenide, Heusler alloys, alloys of manganese-iron, and gadolinium.

The status of the biological construct can be changed by changing the biological construct from a closed state to an open state.

The at least one magnetocaloric actuator can be physically coupled with the biological construct by thermally-coupling the at least one magnetocaloric actuator with a thermally-sensitive biological construct. The operating property of the magnetic apparatus can be changed by changing a DC current supplied to the magnetic apparatus to thereby change the magnitude B of the magnetic field associated with the sample. And, the change in the magnitude B of the magnetic field can cause the temperature of the magnetocaloric actuator to change, which causes the change in the status of the thermally-sensitive biological construct. The temperature change caused to the magnetocaloric actuator can occur without causing a change in status of materials within the sample other than the at least one thermally-sensitive biological construct. The thermally-sensitive biological construct can include an ion channel. The ion channel can be a transient receptor potential cation channel subfamily V member or a transient receptor potential cation channel subfamily M member.

The increasing of the magnitude B of the magnetic field supplied with the DC current can cause the temperature of the magnetocaloric actuator to increase and the temperature of the thermally-sensitive biological construct to increase; and the decreasing of the magnitude B of the magnetic field supplied with the DC current can cause the temperature of the magnetocaloric actuator to decrease and the temperature of the thermally-sensitive biological construct to decrease.

The increasing of the magnitude B of the magnetic field supplied with the DC current can cause the temperature of the magnetocaloric actuator to decrease and the temperature of the thermally-sensitive biological construct to decrease. The decreasing of the magnitude B of the magnetic field supplied with the DC current can cause the temperature of the magnetocaloric actuator to increase and the temperature of the thermally-sensitive biological construct to increase.

DESCRIPTION OF DRAWINGS

FIG. 3A is a graph of a magnetic state M (or magnetic moment) of an implementation of a magnetically manipulatable material that can be in the magnetically manipulatable structure of FIG. 2 versus the sample property, where the sample property is the temperature T;

FIG. 3B is a graph of a magnetic state M (or magnetic moment) of an implementation of a magnetically manipulatable material that can be in the magnetically manipulatable structure of FIG. 2 versus the sample property, where the sample property is the temperature T;

FIG. 4 is a graph of a magnetic state M (or magnetic moment) of an implementation of a magnetically manipulatable material that can be in the magnetically manipulatable structure of FIG. 2 versus the sample property, where the sample property is the magnetic field within the sample;

FIG. 9 is a block diagram of an implementation of the apparatus of FIG. 1 in which the magnetically manipulatable structure is a magnetocaloric actuator that is thermally coupled with a thermally-sensitive biological construct within the sample;

FIG. 13 is a schematic illustration of an implementation of a test apparatus for demonstrating the feasibility of using magnetocaloric materials as thermal actuators of temperature-sensitive biological constructs in genetically-modified cells while in a DC magnetic field;

DETAILED DESCRIPTION

Figure 1:
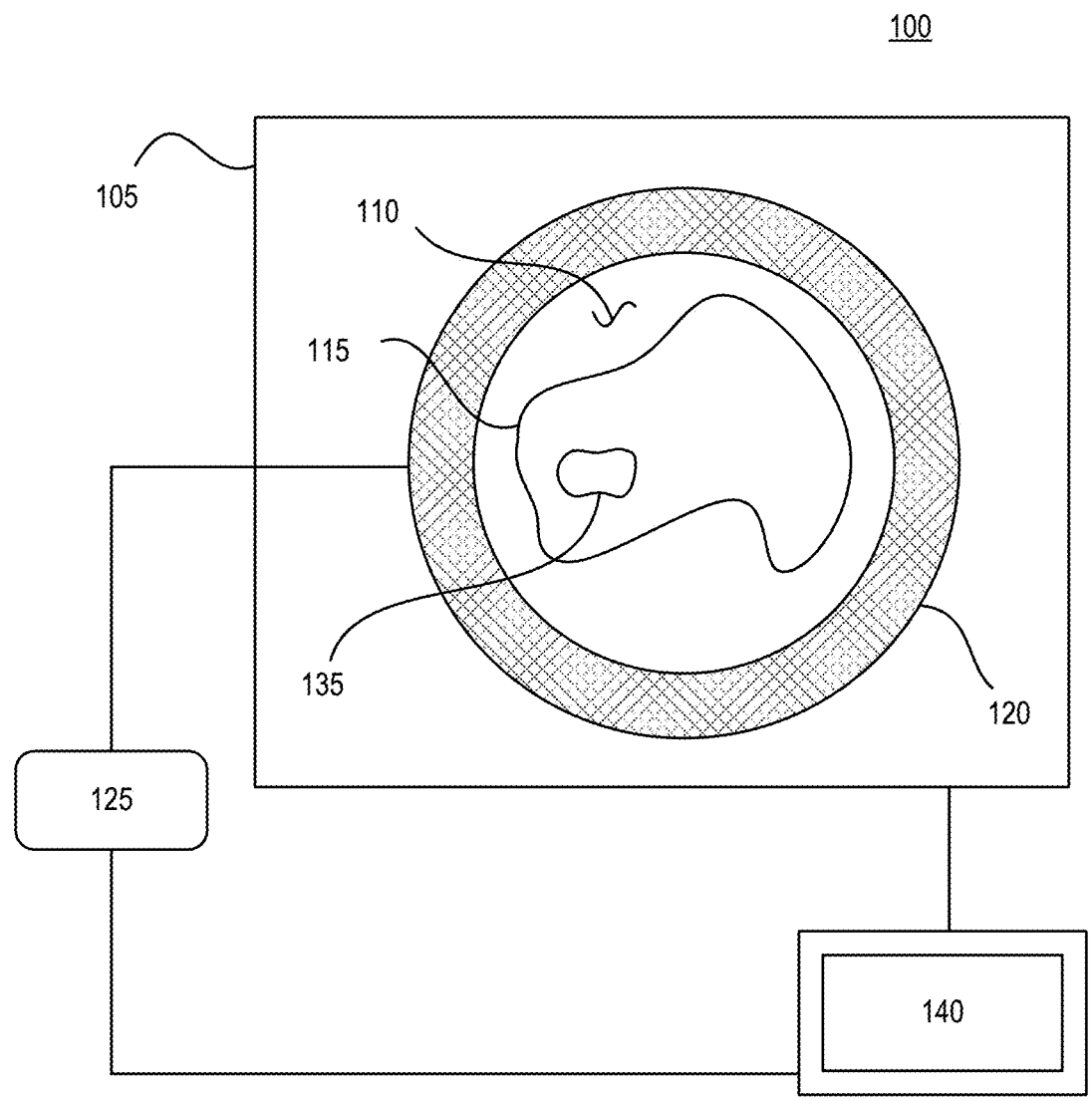
FIG. 1 is a block diagram of an apparatus including a magnetic apparatus having a magnet and a magnetically manipulatable structure embedded in a body of a sample in the magnet.

Referring to FIG. 1, an apparatus 100 is shown that uses a magnetic apparatus 105 to perform one or more functions or operations on a sample 115. The sample 115 is a three-dimensional body. The sample 115 can be a biological or physiological organism or tissue and can be alive. The magnetic apparatus 105 includes a magnet 120 that defines a sample volume 110 that is large enough to accommodate the sample 115. The magnet 120 is configured to create a magnetic field having a magnitude B in the sample 115. The apparatus 100 includes an energy supply 125 connected to the magnet 120 and a control system 140 connected to one or more components (such as the energy supply 125 and the magnet 120) of the magnetic apparatus 105.

The magnetic apparatus 105 includes a magnetically manipulatable structure 135 embedded within the body of the sample 115. The magnetically manipulatable structure 135 is controlled by at least the magnet 120 to affect the function of and operation of the sample 115. The magnetically manipulatable structure 135 includes one or more magnetically manipulatable materials, which can be magnetocaloric materials. The magnetocaloric material is a material that exhibits a transition between a first magnetic state and a second magnetic state in response to a change in a property associated with the sample 115 while the magnetic field having the magnitude B is maintained in the sample 115. This transition can be used to affect the function of or operation of the sample 115. Additionally, the magnetocaloric material experiences a temperature change in response to a changing magnetic field and this temperature change can be used to affect the function of or operation of the sample 115. The magnetically manipulatable material 135 has magnetic properties that can be changed and this change can occur around the temperature of a living organism and also in the presence of large DC magnetic fields of MRI scanners.

While the magnetically manipulatable structure 135 is shown as a monolithic structure in the sample 115 in FIG. 1, it is possible for the magnetically manipulatable structure 135 to be a diffuse or disconnected structure 135 within the sample 115. For example, the structure 135 can include some materials in one region of the sample 115 and other materials in another distinct and separate region of the sample 115.

Magnetocaloric materials can have a sharp and tunable transition of magnetization with respect to changes in an environment in which the magnetocaloric material is placed. For example, if the magnetocaloric material is within a sample (such as the sample 115), then the magnetocaloric material has a sharp and tunable transition of magnetization with respect to changes in one or more properties of the sample when the sample is held at a particular magnetic field. A sample property that can be changed is the temperature or the magnetic field of the sample 115. If the sample 115 is a biological sample, then it is held at a magnetic field that is suitable for the biological sample, and also held at temperatures that are suitable, for example, a typical physiological (body) temperatures and fields of several Teslas (for example, 1 to 20 Teslas). Thus, magnetocaloric materials can be made to be sharply visible or invisible (switchable) in typical magnetic resonance imaging (MRI) machines in response to small changes in properties (for example, temperature or magnetic field) associated with the sample. This makes magnetocaloric materials suitable as sensors and/or labels in the sample. Moreover, the location and properties of these magnetization transitions can be widely tunable in magnetocaloric materials by various materials science techniques of alloying, doping, annealing, for example, thus making the MRI sensor and label design possibilities wide ranging.

Magnetocaloric materials have magnetic properties that provide a close match to the requirements for the design of high contrast ratio switchable and tunable MM labels. More specifically, careful examination of the magnetocaloric materials' magnetic properties reveals that some of them have extremely sharp first-order magnetic phase transitions at typical physiological temperatures and in the presence of the large Tesla-scale magnetic fields typical of MRI settings. Furthermore, these sharp first-order magnetic phase transitions can have a positive or negative slope of magnetization vs. temperature, making them even stronger candidates as versatile materials for high differential contrast switchable MRI labels. Finally, magnetocaloric materials can be engineered and their magnetic properties fine-tuned through materials science techniques such as doping, alloying, thermal treatments and the like to optimize their response under physiological and MM-appropriate conditions. As discussed below, the basic magneto-physical and MM measurements on samples of iron-rhodium (FeRh) are described in order to develop the case for and demonstrate the use of such materials for high differential contrast ratio MRI labels.

For example, the magnetocaloric material is a material selected from the group consisting of iron-rhodium (FeRh), alloys of iron-rhodium, alloys of manganese arsenide, Heusler alloys, alloys of manganese-iron, alloys of lanthanum, iron, and silicon, and gadolinium.

Accordingly, as discussed herein, magnetocaloric materials can be used as tunable and switchable labels and sensors for MRI applications. These magnetocaloric materials have sharp magnetic phase transitions at typical physiological temperatures and in the presence of the large DC magnetic field values associated with MM machines. This means that they have a sharp change in magnetization for a small change in temperature or magnetic field in the experimental settings typical of MM machines, which makes them uniquely suitable as MM contrast agents and sensors. A change of magnetization of the magnetocaloric material can be detected in MM by observing the effect this change in magnetization has on water or biological tissue surrounding the material. Furthermore, the magnetic properties of magnetocaloric materials can be tuned by appropriate materials science technique of alloying, doping, and temperature treatments, for example.

Magnetocaloric materials can be used as sensors of temperature or magnetic field in typical MRI settings of physiological temperature and large bias magnetic fields of 1-20 Tesla. Magnetocaloric materials can be used as switchable MM labels in typical MM settings of physiological temperature and large bias magnetic fields of 1-20 Tesla.

Magnetocaloric materials can be switched on or off in typical MM settings of physiological temperature and large bias magnetic fields of 1-20 Tesla by either a change in magnetic field or a change in temperature or a combination of both. Magnetocaloric materials can have positive or negative slope of magnetization vs. temperature, which means that the labels can be made to be positive labels (can turn on with rise in temperature) or negative labels (can turn off with rise in temperature). This also means that multiple labels can mixed so that some turn on and some off with rise and temperature, and vice versa.

Magnetocaloric materials can be engineered and therefore tuned to have transitions at different magnetic fields and temperatures. This means that these materials can be used as labels so that they are visible or invisible at different magnetic fields of MRI machines.

Figure 2:
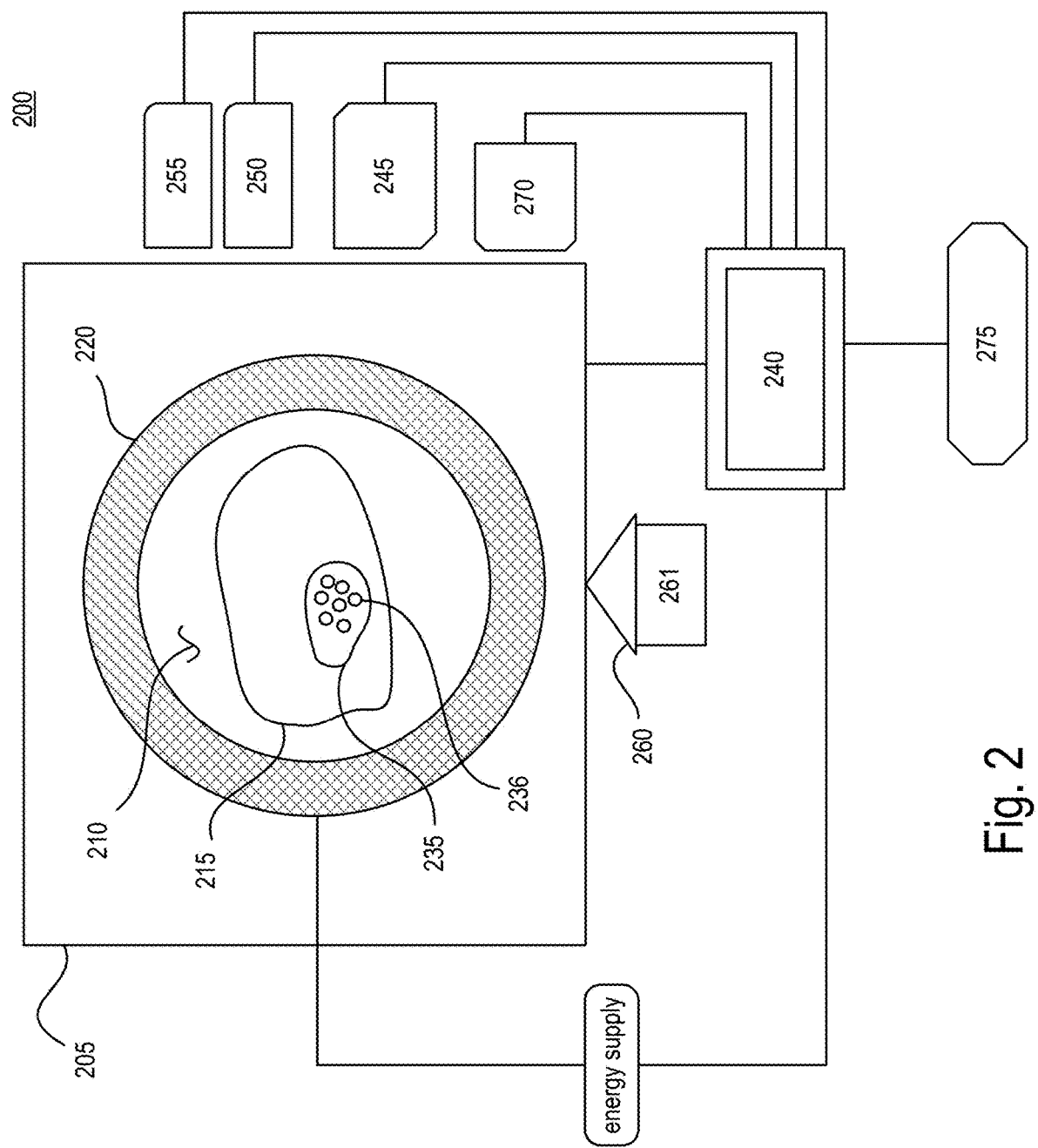
FIG. 2 is a block diagram of an implementation of the apparatus of FIG. 1 in which the magnetically manipulatable structure includes one or more magnetically manipulatable materials, each magnetically manipulatable material being a material that exhibits a transition between a first magnetic state and a second magnetic state in response to a change in a property associated with the sample.

Referring to FIG. 2, in some implementations, the magnetically manipulatable structure 135 is a magnetically manipulatable structure 235 embedded within a sample 215 that is to be imaged within an imaging apparatus 200. The imaging apparatus 200 includes a magnetic apparatus 205 that defines a sample volume 210 that is large enough to accommodate the sample 215 to be imaged. The magnetically manipulatable structure 235 includes and one or more magnetically manipulatable materials 236. The magnetic apparatus 205 includes a magnet 220 that is configured to create a magnetic field having a magnitude B in the sample 215. Each magnetically manipulatable material 236 is a material that exhibits a transition between a first magnetic state and a second magnetic state in response to a change in a property associated with the sample while the magnetic field having the magnitude B is maintained in the sample. Thus, each magnetically manipulatable material 236 can be a magnetocaloric material.

The apparatus 200 includes an energy supply 225 connected to the magnet 220. The magnet 220 can be formed from electrically conductive wire coils through which current from the energy supply 225 is passed. The energy supply 225 can provide a direct current (DC) to the wire coils, which means that the energy supply 225 provides a constant voltage or current to the wire coils of the magnet 220. Thus, the energy supply 225 can, for example, include an alternating current (AC) generator equipped with a device to produce the direct current, a device that converts AC to DC, or batteries to provide DC. In some implementations, the magnet 220 can be a superconducting magnet.

In some implementations, the magnetic field magnitude B is greater than 0.5 Tesla. In other implementations, the magnetic field magnitude B is in a range of 1-20 Tesla. The magnitude B of the magnetic field is limited by the design of the magnet 220. Thus, for example, if the magnet 220 is a superconducting magnet, then the magnitude B can be as large as 20 Tesla. The large value of the magnitude B allows for higher-quality imaging, and the superconductivity enable the imaging apparatus to work more efficiently.

In some implementations, the first magnetic state of the magnetically manipulatable material 236 is an antiferromagnetic state or a paramagnetic state, which means that the magnetically manipulatable material 236 is so weakly magnetic that it is considered to be non-magnetic. In an antiferromagnetic state, adjacent moments that behave as tiny magnets spontaneously align themselves into opposite, or antiparallel, arrangements throughout the magnetically manipulatable material 236 so that the material 236 exhibits almost no gross external magnetism. In antiferromagnetic materials, the magnetism from magnetic moments oriented in one direction is canceled out by the set of magnetic moments that are aligned in the reverse direction. In a paramagnetic state, some of the atoms or ions in the magnetically manipulatable material 236 have a net magnetic moment due to unpaired electrons in partially filled orbitals; however, the individual magnetic moments do not interact magnetically, and the magnetization is zero when a field is removed. In the presence of a field, there is now a partial alignment of the atomic magnetic moments in the direction of the field, resulting in a net positive magnetization and positive susceptibility.

In some implementations, the second magnetic state of the magnetically manipulatable material 236 is a ferromagnetic state or a ferrimagnetic state, which means that the material is considered to be magnetic. In a ferromagnetic state, the spins in the material 236 exhibit parallel alignment of moments resulting in large net magnetization even in the absence of a magnetic field. In a ferrimagnetic state, the opposing moments of the spins in the material 236 are unequal and a spontaneous magnetization remains in the absence of a magnetic field.

If the sample 215 is a living physiological or biological tissue, then the magnetically manipulatable material 236 exhibits the transition while the temperature in the sample is at a physiological temperature, for example, between 270 and 370 Kelvin (K).

The property associated with the sample 215 that is altered can be a temperature. The transition occurs in response to a change in temperature that is less than a fraction of the temperature of the sample 215. For example, the change in temperature can be a factor of ten times smaller than the temperature of the sample 215. Thus, if the temperature of the sample 215 is about 270-370 K, then the temperature change can be about 10-40 K.

The property associated with the sample 215 that is altered can be a magnetic field of the sample. In this case, the transition occurs in response to a change in a magnitude of a magnetic field ($\Delta B$), where the change in magnitude $\Delta B$ that is substantially smaller than the magnitude B of the magnetic field. The change in magnitude is substantially smaller than the magnitude B if it is a fraction of the magnitude B, an order of magnitude smaller than the magnitude B, or at least an order of magnitude smaller than the magnitude B.

The imaging apparatus 200 also includes a sample property scanning system 245 configured to change the property of the sample 215 while the magnetic field having magnitude B is maintained in the sample 215. The sample property scanning system 245 therefore acts to cause the transition in the magnetically manipulatable material 236.

In some implementations, the sample property scanning system 245 includes a temperature scanning system for changing, as the property, a temperature of the sample 215. The temperature scanning system includes an apparatus thermally connected to the sample 215. The thermally connected apparatus includes an induction heater that operates at either a medium frequency or a radio frequency range and includes a controller, and a heat inductor. The heat inductor can be a heating coil.

In other implementations, the sample property scanning system 245 includes a magnetic scanning system for changing, as the property, a magnetic field of the sample 215. The magnetic scanning system includes a magnetic source that is configured to change the magnetic field of the sample 215.

In some implementations, the magnetic apparatus 205 is a magnetic resonance imaging (MRI) apparatus. In this case, imaging apparatus 200 can include, in addition to the magnet 220 shown in FIG. 2, one or more gradient magnets 250 configured to produce a variable magnetic field that ranges in strength an amount that is much less than (for example, one hundredth of) the magnitude B. This variable magnetic field can permit different parts of the sample 215 to be scanned. The imaging apparatus 200 can also include an electromagnetic source 255 configured to produce a varying electromagnetic field having a range of magnetic field magnitude that is much less than (for example, one hundredth of) the magnitude B. The varying electromagnetic field can be a radiofrequency field and can be produced by a set of coils that transmit the radiofrequency waves into specific regions of the sample 215.

If the magnetically manipulatable material 236 is not inherently found in the sample 215, then it can be added to the sample 215. For example, the imaging apparatus 200 can include a delivery (or injection) apparatus 260 configured to transport the magnetically manipulatable material 236 from a source 261 of the material into the sample 215. The magnetically manipulatable material 236 can be in the form of a plurality of spatially-separated particles. The particles are dispersed throughout at least one region of interest within the sample. If the sample 215 is a living organism, then the size of the particles can be on the order of the size of cells within the sample 215. For example, the size of the particles is on the order of micrometers, for example, 1-10 micrometers ($\mu m$). In some implementations, each particle has a microscopic size (which means it is only viewable with the use of a microscope).

The particles of the magnetically manipulatable material 236 can be prepared prior to delivery into the sample 215 to be in a suitable state for operation or use in the sample 215.

If the sample 215 is a living organism, the sample 215 is held at a physiological temperature to maintain the organism in a living state.

The imaging apparatus 200 includes a detector 270 that detects a signal produced as a result of the interaction between the magnetic field and the sample 215. The imaging apparatus 200 can also include some sort of output device 275 such as a display. Additionally, the imaging apparatus includes a control system 240 connected to the magnetic apparatus 205. The control system 240 is also connected to the other components of the imaging apparatus 200 such as the property scanning system 245, the electromagnetic source 255, the gradient magnets 250, the injection apparatus 260, the detector 270, the display 275, and the energy supply 225. The control system 240 is configured to: receive data output from the detector 270, the output relating to the detected signal; analyze the received data; and estimate the sample property based on the analysis. The control system 240 is also configured to create an image of the sample 215 at the display 275 based on the analysis.

The detector 270 detects the signal produced as a result of the interaction between the magnetic field and the sample 215 by detecting a signal produced by tissue within the sample 215 that is in proximity to the magnetically manipulatable material 236. The signal produced by tissue within the sample 215 that is in proximity to the magnetically manipulatable material 236 includes electromagnetic radiation generated from protons within the sample 215 in proximity to the magnetically manipulatable material 236.

The magnetically manipulatable material 236 remains magnetically unsaturated while the magnetic field having the magnitude B exists in the sample 215. This means that the magnetically manipulatable material 236 is capable of exhibiting a transition between the first magnetic state and the second magnetic state even while the magnetic field having the magnitude B exists in the sample 215.

In some implementations, the magnetically manipulatable structure 235 includes one or more different magnetically manipulatable materials 236 or magnetocaloric materials. In these implementations, each different magnetically manipulatable material 236 in the structure can have a transition that occurs in response to a distinct change in the property of the sample 215. For example, a first magnetically manipulatable material 236 has a transition from the first magnetic state to the second magnetic state that occurs in response to an increase in the sample property; and a second magnetically manipulatable material 236 has a transition from the first magnetic state to the second magnetic state that occurs in response to a decrease in the sample property. As another example, a first magnetically manipulatable material 236 has a transition from the first magnetic state to the second magnetic state that occurs in response to an increase in the sample property; and a second magnetically manipulatable material 236 has a transition from the second magnetic state to the first magnetic state that occurs in response to an increase in the sample property. As a still further example, a first magnetically manipulatable material 236 has a transition between the first magnetic state and the second magnetic state that occurs in response to a change in a first sample property; and a second magnetically manipulatable material 236 has a transition between the first magnetic state and the second magnetic state that occurs in response to a change in a second sample property that is distinct from the first sample property.

In other implementations, the transition from the first magnetic state to the second magnetic state occurs in a first range of values of the property as the property is increased; the transition from the second magnetic state to the first magnetic state occurs in a second range of values of the property as the property is decreased; and the first range of values is distinct from the second range of values.

FIG. 3A shows a magnetic state M (or magnetic moment) of the magnetically manipulatable material 236 versus the sample property, where the sample property is the temperature T of the sample 215. In the implementation shown in FIG. 3A, the magnetically manipulatable material 236 transitions from a first magnetic state 300 to a second magnetic state 305 at a transition temperature T(tr). In this implementation, the first magnetic state 300 is magnetic, for example, ferromagnetic or ferrimagnetic, and the second magnetic state 305 is non-magnetic, for example, an antiferromagnetic or a paramagnetic. Moreover, this transition occurs while the magnetic field having the magnitude B is maintained in the sample 215, where the magnitude B is a value between 1-10 T. The transition temperature T(tr) can be between 270 K and 370 K or around 310 K.

FIG. 3B shows a magnetic state M (or magnetic moment) of the magnetically manipulatable material 236 versus the sample property, where the sample property is the temperature T of the sample 215. In the implementation shown in FIG. 3B, the magnetically manipulatable material 236 transitions from a first magnetic state 310 to a second magnetic state 315 at a transition temperature T(tr). In this implementation, the first magnetic state 310 is non-magnetic, for example, antiferromagnetic or paramagnetic, and the second magnetic state 315 is magnetic, for example, ferromagnetic or ferrimagnetic. Moreover, this transition occurs while the magnetic field having the magnitude B is maintained in the sample 215, where the magnitude B is a value between 1-10 T. The transition temperature T(tr) can be between 270 K and 370 K or around 310 K.

FIG. 4 shows a magnetic state M (or magnetic moment) of the magnetically manipulatable material 236 versus the sample property, where the sample property is the magnetic field (represented by the magnitude B) within the sample 215. In the implementation shown in FIG. 4, the magnetically manipulatable material 236 transitions from a first magnetic state 400 to a second magnetic state 405 at a first transition magnetic field magnitude B1(tr), and from the second magnetic state 405 to a third magnetic state 410 at a second transition magnetic field magnitude B2 (tr). In this implementation, the first magnetic state 400 is non-magnetic, for example, antiferromagnetic or paramagnetic; the second magnetic state 405 is also non-magnetic, and the third magnetic state 410 is magnetic. Moreover, these transitions occur while the temperature within the sample 215 is maintained at a temperature T, which can have a value between 270 K and 370 K or around 310 K. The magnitude B1(tr) can be any value between 1-10 T, for example 4 T, and the magnitude B2(tr) can be any other value between 1-10 T, for example, 5 T.

Figure 5A:
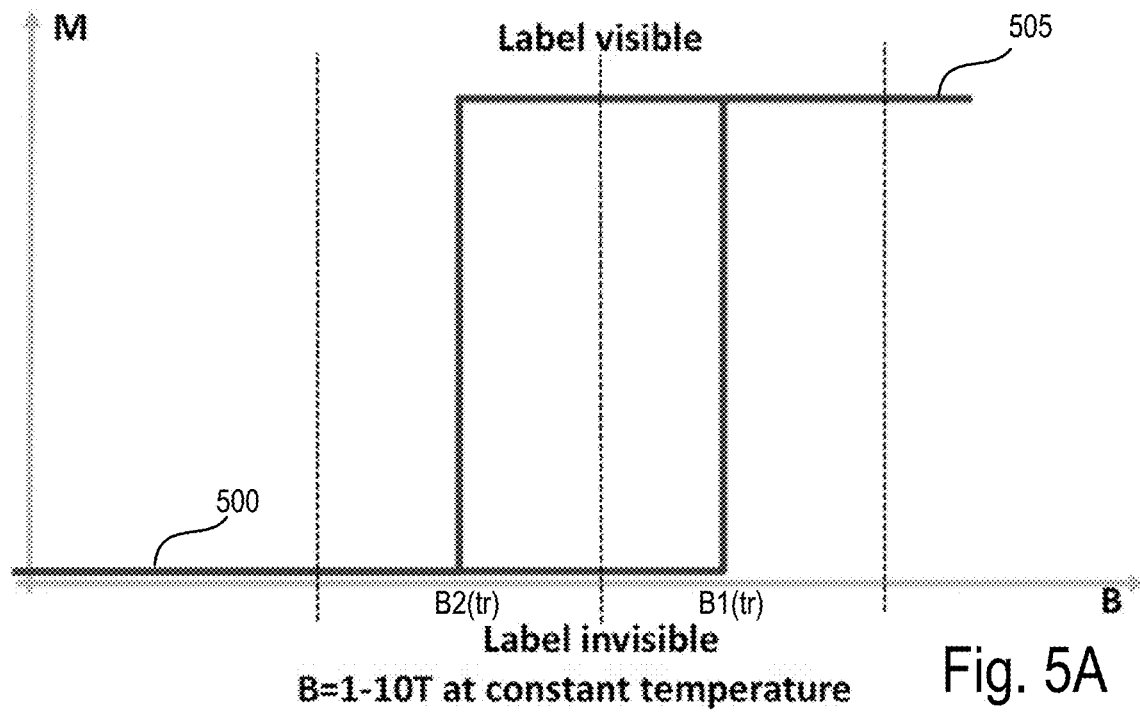
FIG. 5A is a graph of a magnetic state M (or magnetic moment) of an implementation of a magnetically manipulatable material versus the sample property, where the sample property is the magnetic field within the sample.

FIG. 5A shows a magnetic state M (or magnetic moment) of the magnetically manipulatable material 236 versus the sample property, where the sample property is the magnetic field (represented by the magnitude B) within the sample 215, while maintaining the sample 215 at a constant temperature T. The transition from the first magnetic state 500 to the second magnetic state 505 occurs at a magnitude B1(tr) while the magnitude B is increased. On the other hand, the transition from the second magnetic state 505 to the first magnetic state 500 occurs at a different magnitude B2(tr) while the magnitude is decreased. The magnitude B2(tr) is less than the magnitude B1(tr). This is because of the hysteresis effect (in which the physical effect, that is, the magnetic state M, on the sample 215 is retarded or changed depending how the sample property is changed).

Figure 5B:
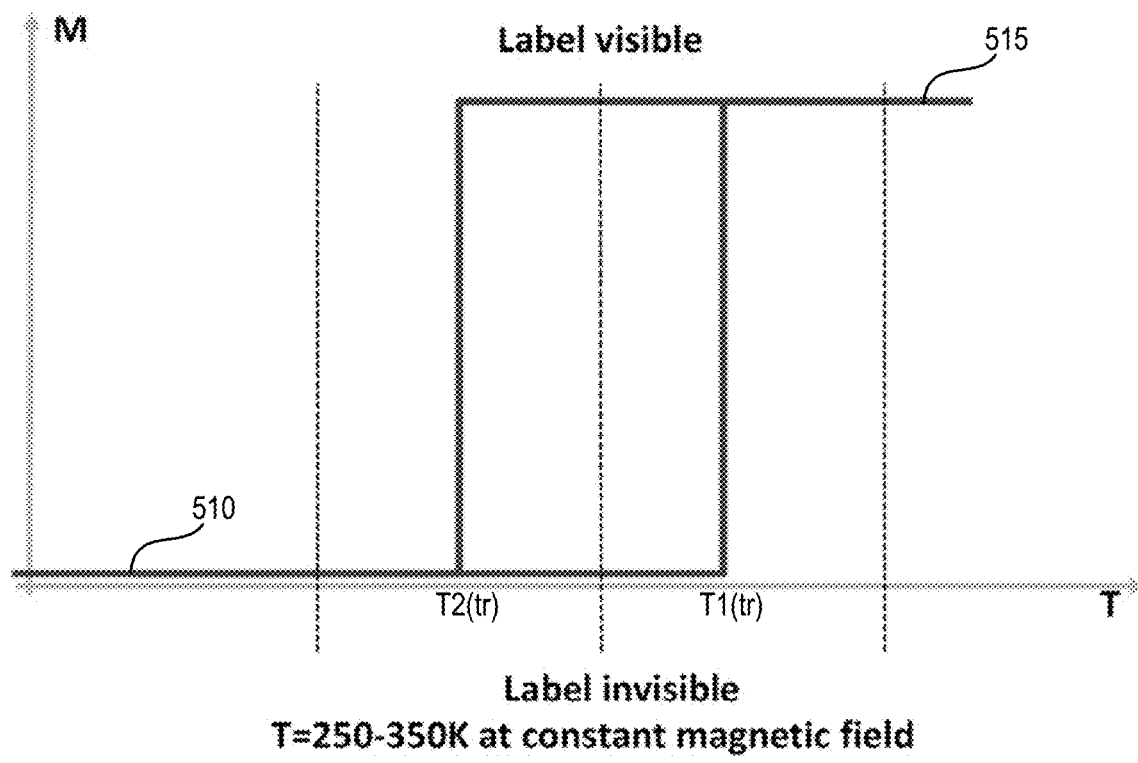
FIG. 5B is a graph of a magnetic state M (or magnetic moment) of an implementation of a magnetically manipulatable material versus the sample property, where the sample property is the temperature within the sample.

FIG. 5B shows a magnetic state M (or magnetic moment) of the magnetically manipulatable material 236 versus the sample property, where the sample property is the temperature (represented by T) within the sample 215, while maintaining the sample 215 at a constant magnetic field magnitude B. The transition from the first magnetic state 510 to the second magnetic state 515 occurs at a temperature T1(tr) while the temperature T is increased. On the other hand, the transition from the second magnetic state 515 to the first magnetic state 510 occurs at a different temperature T2(tr) (which is less than the temperature T1(tr)) while the temperature T is decreased because of the hysteresis effect.

Furthermore, it is possible that the magnetically manipulatable material 236 only exhibits a transition in response to a change in two sample properties.

As mentioned above, and referring to FIG. 6A, the magnetically manipulatable structure 235 can include a plurality of different magnetically manipulatable materials 236 (that is, two or more magnetically manipulatable materials) within the sample 215. In this example, there are two magnetically manipulatable materials 236a and 236b contained or embedded within the sample 215. FIG. 6B shows an example of a graph of a magnetic state M (or magnetic moment) of the two magnetically manipulatable materials 236a, 236b within the sample 215 versus the sample property, where the sample property is the magnetic field (represented by the magnitude B) within the sample, while maintaining the sample 215 at a constant temperature T. In this implementation, the two magnetically manipulatable materials 236a, 236b have different transition points in response to a change in the magnetic field magnitude B.

The behavior of the first magnetically manipulatable material 236a is shown in the red graph 602 and the behavior of the second magnetically manipulatable material 236b is shown in the green graph 612. The first magnetically manipulatable material 236a transitions from its first magnetic state 600 to its second magnetic state 605 at a magnetic field magnitude B1(tr) as the magnetic field magnitude B is being increased while the first magnetically manipulatable material 236a transitions from its second magnetic state 605 to its first magnetic state 600 at a magnetic field magnitude B2(tr) as the magnetic field magnitude B is being decreased. The second magnetically manipulatable material 236b transitions from its first magnetic state 610 to its second magnetic state 615 at a magnetic field magnitude B3(tr) as the magnetic field magnitude B is being increased while the second magnetically manipulatable material 236b transitions from its second magnetic state 615 to its first magnetic state 610 at a magnetic field magnitude B4(tr) as the magnetic field magnitude B is being decreased. These transitions points B1(tr), B2(tr), B3(tr), and B4(tr) are distinct from each other. For example, if the magnetic field magnitude B generally remains between 1-10 T and the temperature at which the sample 215 is held is about 310 K, then the transition point B1(tr) can be 4.4 T, the transition point B2(tr) can be 3.7 T, the transition point B3(tr) can be 6.7 T, and the transition point B4(tr) can be 5.7 T. In this example, both of the magnetically manipulatable materials 236a, 236b are non-magnetic below 3.7 T, both of the magnetically manipulatable materials 236a, 236b are magnetic above 6.7 T, and the first magnetically manipulatable material 236a is magnetic while the second manipulatable material 236b is non-magnetic at 4.7 T.

Figure 7A:
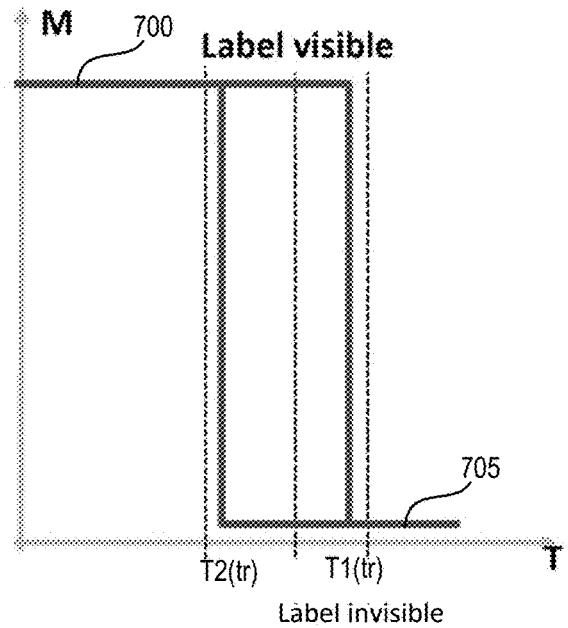
FIG. 7A is a graph showing an implementation of a magnetically manipulatable material that transitions from a magnetic to a non-magnetic state with a rise in temperature.

In some implementations, the magnetically manipulatable material 236 transitions from a magnetic to a non-magnetic state with a rise in the sample property. For example, as shown in FIG. 7A, a first magnetically manipulatable material transitions from a magnetic state 700 to a non-magnetic state 705 at the transition temperature T1(tr) as the sample property of temperature T is increased while the first magnetically manipulatable material transitions from the non-magnetic state 705 to the magnetic state 700 at the transition temperature T2(tr) as the sample property of temperature T is decreased. In this example, the magnetic field magnitude B is held constant. As an example, the material Iron-Lanthanum-Silicon (Fe—La—Si) behaves in this manner.

Figure 7B:
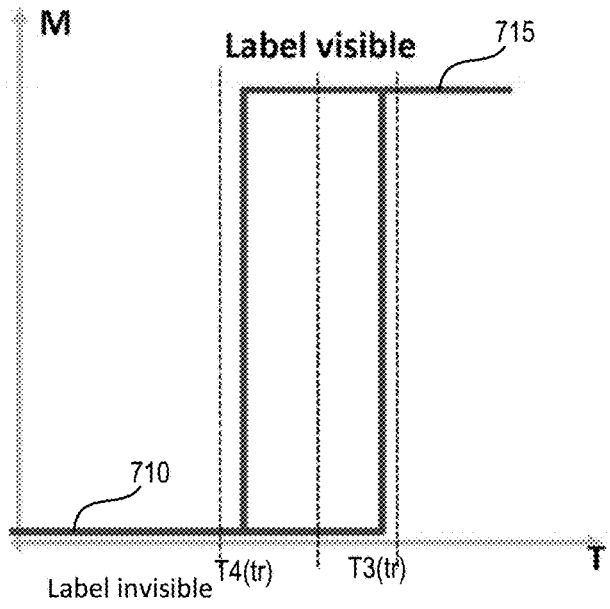
FIG. 7B is a graph showing an implementation of a magnetically manipulatable material that transitions from a non-magnetic to a magnetic state with a rise in temperature.

In other implementations, the magnetically manipulatable material 236 transitions from a non-magnetic to a magnetic state with a rise in the sample property. For example, as shown in FIG. 7B, a second magnetically manipulatable material transitions from a non-magnetic state 710 to a magnetic state 715 at the transition temperature T3(tr) as the sample property of temperature T is increased while the second magnetically manipulatable material transitions from the magnetic state 715 to the non-magnetic state 710 at the transition temperature T4(tr) as the sample property of temperature T is decreased. In this example, the magnetic field magnitude B is held constant. For example, the material FeRh behaves in this manner.

Figure 6A:
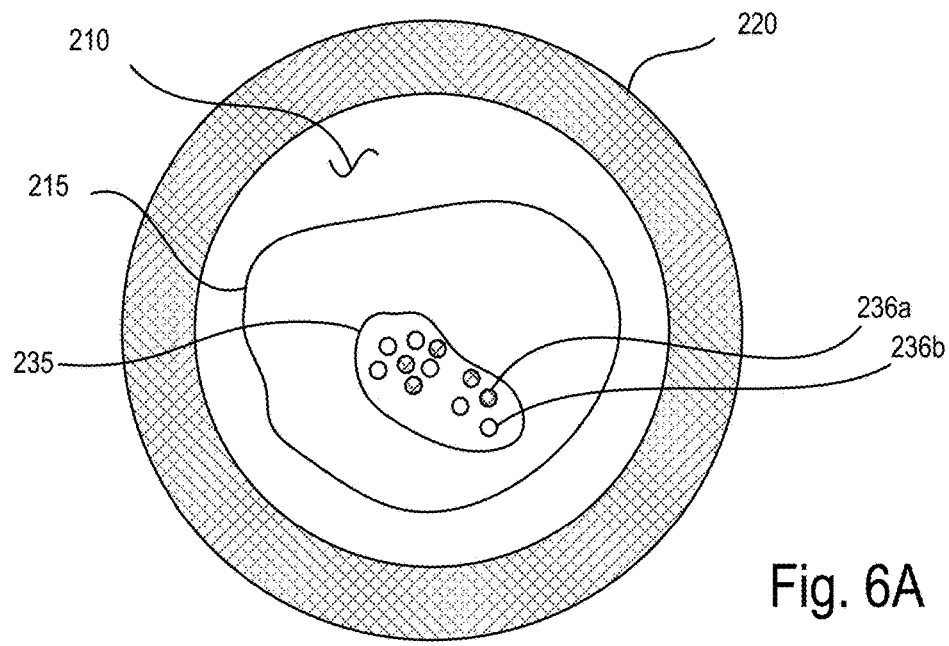
FIG. 6A is a schematic representation of a sample in which the magnetically manipulatable structure includes a plurality of different magnetically manipulatable materials.
Figure 6B:
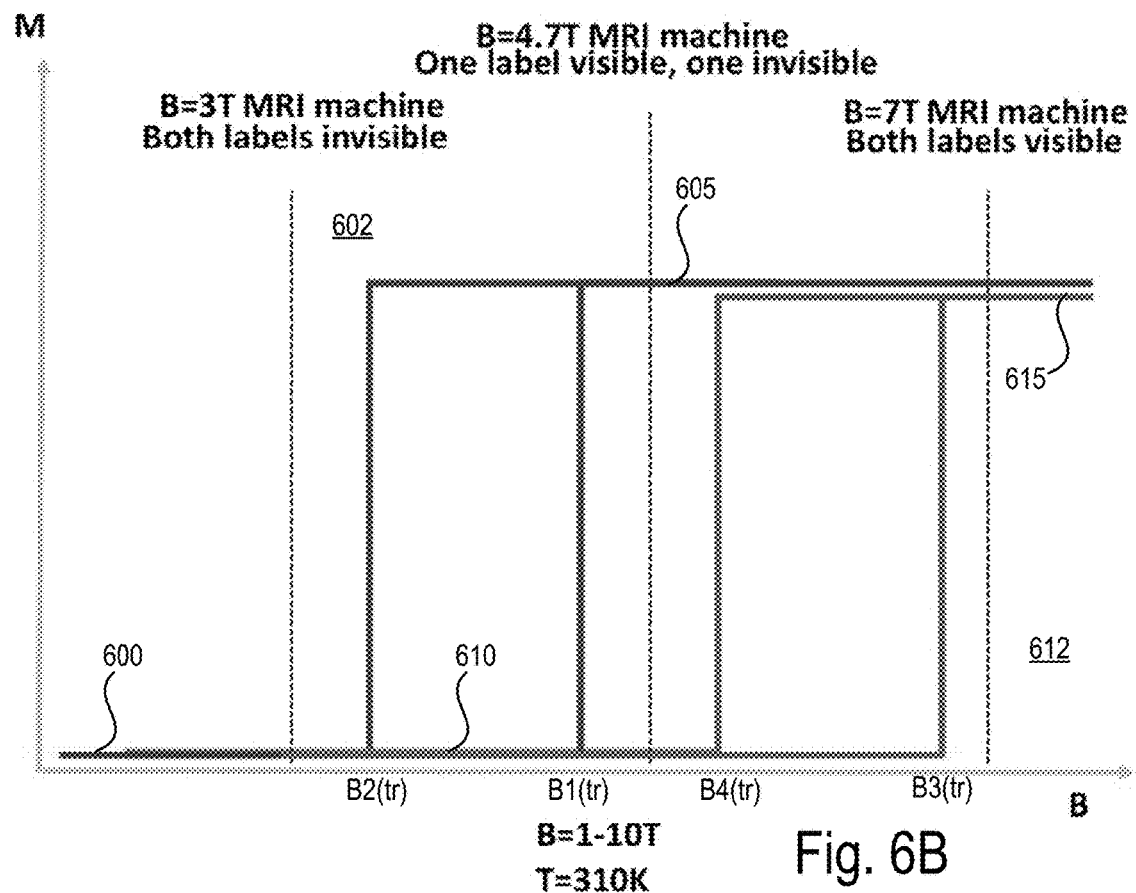
FIG. 6B is a graph of a magnetic state M (or magnetic moment) of the two magnetically manipulatable materials of FIG. 6A within the sample versus the sample property, where the sample property is the magnetic field within the sample.
Figure 8:
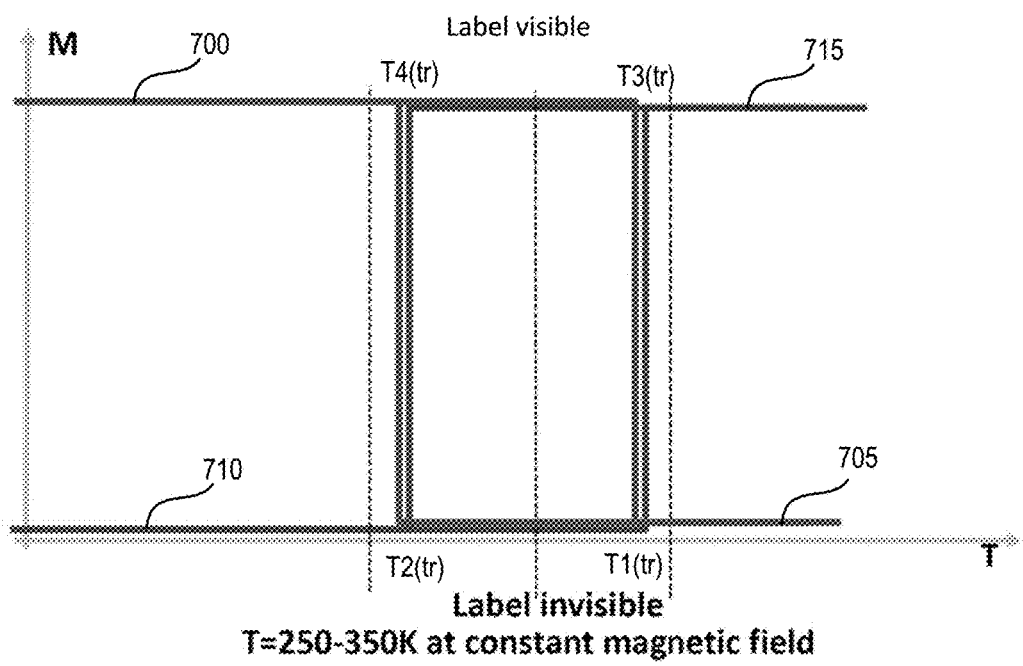
FIG. 8 is a graph of a magnetic state M of the first and the second magnetically manipulatable materials of FIGS. 7A and 7B within the sample versus temperature.

If both the first and the second magnetically manipulatable materials of FIGS. 7A and 7B are within the sample 215, such as shown in FIG. 6A, then an exemplary combined transition graph is shown in FIG. 8 in which the transition temperature T3(tr) is equal to the transition temperature T1(tr) and the transition temperature T4(tr) is equal to the transition temperature T2(tr). In this implementation, the first and second magnetically manipulatable materials 236a, 236b can be switched on an off (that is, transitioned from the magnetic state to the non-magnetic state) in opposite manners. For example, the second magnetically manipulatable material 236b is magnetic and the first magnetically manipulatable material 236a is non-magnetic above the transition temperature T3(tr) (and T1(tr)) while the first magnetically manipulatable material 236a is magnetic and the second magnetically manipulatable material 236b is non-magnetic below the transition temperature T4(tr) (and T4(tr)). In this example, the temperature can be adjusted in a range of 250 K to 350 K.

While only two magnetically manipulatable materials 236a and 236b are discussed above, it is possible for the magnetically manipulatable structure 235 to include more than two different types of these materials.

Referring to FIG. 9, in other implementations, the magnetically manipulatable structure 135 is a magnetically manipulatable structure 935 embedded within a sample 915 of an apparatus 900. The apparatus 900 is designed to use magnetocaloric materials as physical actuators of biological constructs in genetically-modified cells while in a DC magnetic field. For simplicity, components shown in FIG. 9 are merely in block diagram form and are not to scale. A change to a property of the magnetocaloric material causes a change in the status of the biological construct because the magnetocaloric material is physically coupled with the biological construct. A physical coupling means that there is a coupling that is based on an exchange of matter or energy. For example, the physical coupling could be a thermal coupling. As another example, the physical coupling could be an electromagnetic coupling. The property of the magnetocaloric material that can be changed can be its magnetic state. The property of the magnetocaloric material that can be changed can be its temperature.

In some implementations, and as described herein, the property of the magnetocaloric material that is changed is the temperature, and the temperature of the magnetocaloric material is changed by a change in magnitude B of the magnetic field applied to the sample 915. In these implementations, the physical coupling between the magnetocaloric material and the biological construct is a thermal coupling and the biological construct is a thermally-sensitive biological construct.

The apparatus 900 includes a magnetic apparatus 905 that defines an actuation volume 910 that is large enough to accommodate the sample 915. The magnetic apparatus 905 includes a magnet 920 that is configured to create a magnetic field having a magnitude B in the sample 915 when supplied with a DC current from a DC energy supply 925.

The apparatus 900 includes at least one thermally-sensitive biological construct 930 within the sample 915. The magnetically manipulatable structure 935 is a magnetocaloric actuator 935 thermally coupled with the thermally-sensitive biological construct 930. While one construct 930 and one actuator 935 is shown, it is possible to have a plurality of constructs 930 or a plurality of actuators 935 associated with each construct. Thermal coupling between two elements means that the heat is freely conducted between those two elements. Thus, heat is able to be thermally conducted between the biological construct 930 and the actuator 935. Thermal coupling between two elements can mean that the two elements are near enough to each other so that heat does not dissipate substantially into the sample 915 before being conducted between the two elements. Thermal coupling between two elements can mean that the two elements have relative sizes that are complementary so that heat transfer between the two elements is enabled.

A change in the magnitude B of the magnetic field supplied with the DC current from the supply 925 to the magnet 920 causes the temperature of the magnetocaloric actuator 935 to change, and this change causes a change in a status of the thermally-sensitive biological construct 930.

The apparatus 900 therefore operates under the application of a DC magnetic field, or a magnetic field that is very close to DC. That is, the magnetic field changes relatively slowly at the location of the actuator 935.

The apparatus 900 also includes a control system 940 connected to the DC energy supply 925 to control the operation of the DC energy supply 925.

The magnetocaloric actuator 935 can include one or more magnetically manipulatable materials 936i. The magnetically manipulatable material 936i exhibits a transition between a first magnetic state and a second magnetic state in response to the change in the magnitude B of the magnetic field produced by the magnet 920. For example, the magnetically manipulatable material 936i of the actuator 935 exhibits the transition while the temperature in the sample 915 is between 270 and 370 K. The magnetically manipulatable material 936i of the actuator 935 can include a material selected from the group consisting of iron-rhodium (FeRh), alloys of iron-rhodium, alloys of manganese arsenide, Heusler alloys, alloys of manganese-iron, alloys of lanthanum, iron, and silicon, and gadolinium.

Each magnetically manipulatable material 936i is a spatially-separated particle having a size that is large enough to retain heat long enough to cause the change in status in the thermally-sensitive biological construct 930. For example, a cell in a living organism can be between 1-50 μm in diameter. If the biological construct 930 is on the order of a nanometer (nm), then the magnetocaloric actuator 935 can have a size on the order of about 1-100 μm.

The sample 915 can be a region of a live human body. In this implementation, the magnetically manipulatable material 936i of the actuator 935 exhibits the transition while the temperature in the live human body region is at a human body temperature. In some implementations, the sample 915 is a living organism and the sample 915 is held at a physiological temperature to maintain the organism in a living state.

The transition between the first magnetic state and the second magnetic state of the magnetically manipulatable material 936i can occur in response to a change in a magnitude of a magnetic field that is substantially smaller than the overall magnitude B of the magnetic field produced by the magnet 920.

The temperature change caused to the magnetocaloric actuator 935 occurs without causing a change in status of materials within the sample 915 other than the at least one thermally-sensitive biological construct 930. In this way, the apparatus 900 is able to finely heat and cool in local areas of the sample 915 without causing large-scale heating or cooling to other areas of the sample 915.

In some implementations, the magnet 920 includes electrically conductive wire coils through which current from the DC energy supply 925 is passed. Thus, the DC energy supply 925 provides the DC current supplied to the wire coils. In some implementations, the magnet 920 is a superconducting magnet. And, the magnetic apparatus 905 can be a magnetic resonance imaging apparatus.

Moreover, the magnetic field magnitude B is greater than 0.5 Tesla or in a range of 1-20 Tesla. The magnitude B of the magnetic field can be in a range that does not cause any detrimental changes to the sample 915. That is, the sample 915 does not deteriorate or degrade due to the magnitude B of the magnetic field that is created.

The temperature change dT that occurs in the magnetocaloric actuator 935 is governed by the following equation.

$$dT = -\frac{T}{C_B} \times \left(\frac{\partial M}{\partial T}\right)_B dB,$$

where T is the temperature of the magnetocaloric actuator 935, $C_B$ is the heat capacity of the magnetocaloric actuator 935, $\partial M/\partial T$ is the slope of the magnetization M of the magnetocaloric actuator 935 versus the temperature T at the specific magnetic field B, and dB is the change in magnetic field applied to the magnetocaloric actuator 935 by the magnet 920. The temperature T of the actuator 935 changes as the magnetic field magnitude B changes. Moreover, the slope $\partial M/\partial T$ is an inherent property of the magnetocaloric actuator 935. As an example, the magnetocaloric actuator temperature change dT is at least 5° C. for a change in magnitude of the magnetic field dB between 1-20 T.

In another example, if the magnetic field B supplied by the magnet 920 changes from 0 T to 2 T, then the value of dB is 2 T. As another example, if the magnetic field B supplied by the magnet 920 changes from 3 T to 5 T, then the value of dB is 2 T. The magnetically manipulatable materials 936i that are selected for the magneto-caloric actuator 935 are selected to provide a temperature change dT for as small a change in magnetic field B. Thus, the value of $\partial M/\partial T$ for the magnetically manipulatable materials 936i is as large as possible or at a maximum at typical physiological (biological) temperatures T (for example, around 37° C.). In particular, materials 936i that have suitable values of $\partial M/\partial T$ include gadolinium and FeRh. Other materials can have a large value of $\partial M/\partial T$ at temperatures T that are not typical physiological or biological temperatures, and those other materials would not be suitable for use in a physiological or biological sample 915.

If the magnetic apparatus 205 is an MRI machine, then the apparatus 900 can include one or more of the other components for operating the MRI machine. For example, the apparatus 900 can also include one or more of the property scanning system 245 (which is used to scan or change the magnetic field of the sample 915 in this implementation), the electromagnetic source 255, the gradient magnets 250, the detector 270, and the display 275.

Figure 10B:
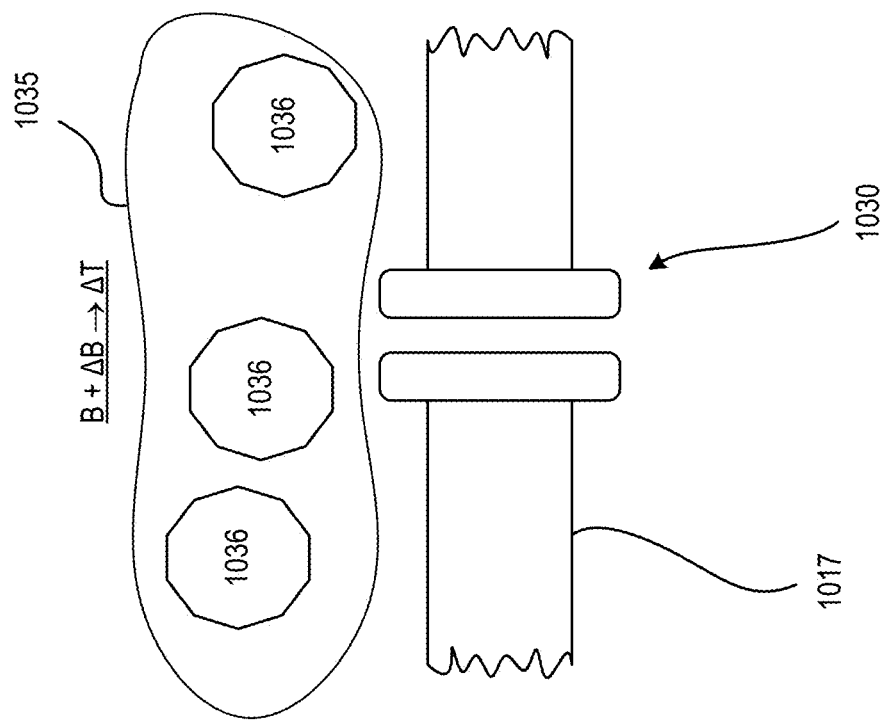
FIGS. 10A and 10B are schematic illustrations of an implementation in which the thermally-sensitive biological construct of FIG. 9 is an ion channel positioned along a cellular structure of the sample, the magnetocaloric actuator includes a plurality of magnetically manipulatable materials near the ion channel; and the ion channel has a closed status (FIG. 10A) or an open status (FIG. 10B)
Figure 10A:
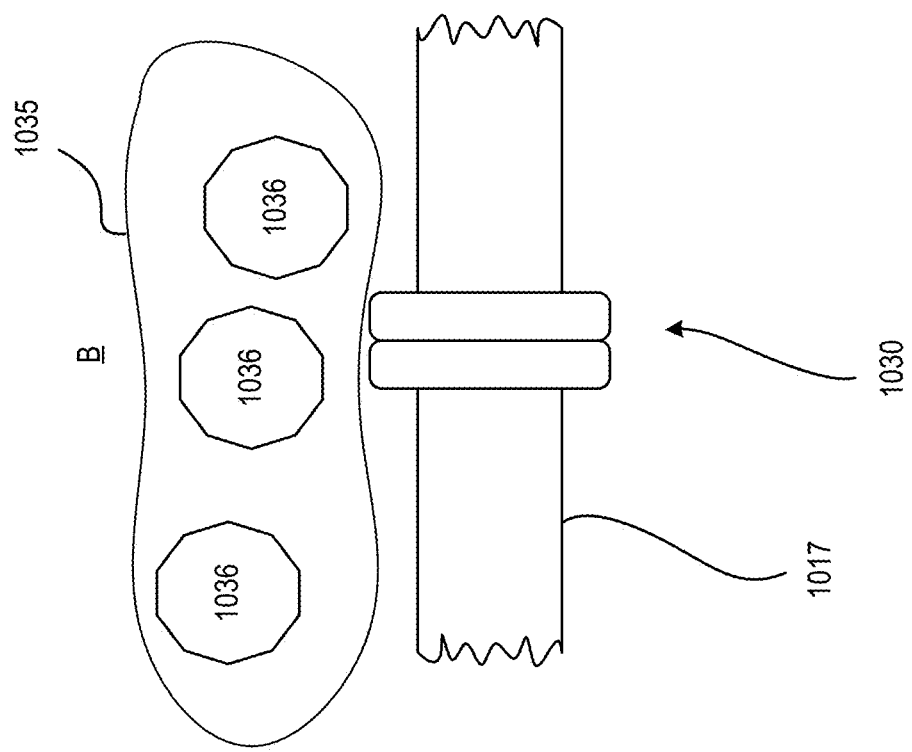

FIGS. 10A and 10B are block diagrams of an implementation in which the at least one thermally-sensitive biological construct 930 within the sample 915 is an ion channel 1030 positioned along a cellular structure 1017 (for example, a cell membrane) of the sample 915. The at least one magnetocaloric actuator 1035 is a magnetocaloric actuator 1035 that includes a plurality of magnetically manipulatable materials 936i near the ion channel 1030. The ion channel 1030 has a status that is either closed (FIG. 10A) or open (FIG. 10B). For example, when closed, the ion channel 1030 blocks other elements (such as molecules, ions, or atoms) nearby and within the sample 915 from passing through the cellular structure 1017. When open, the ion channel 1030 permits these other nearby elements (such as molecules, ions, or atoms) to freely pass through the cellular structure 1017 as long as the opening is large enough to accommodate the size of the element.

Temperature sensitive ion channels 1030 can be integrated into the cell membrane (the cellular structure 1017) using a suitable technique such as cloning or genetic engineering. For example, the ion channel 1030 can be genetically engineered into the cellular structure 1017. This means that the ion channel 1030 may not be present in the wild-type or non-engineered cellular structure 1017 of the sample 915. The cellular structure 1017 can be genetically altered through the exogenous delivery of a portion of deoxyribonucleic acid (DNA) comprising a gene that expresses the ion channel 1030 in the sample 915. For example, transgenic expression of a temperature-activated ion channel in a cell comprising the sample 915 leads to the insertion of the ion channel 1030 into the cell membrane, identified as the cellular structure 1017.

In some implementations, the ion channel 1030 is a transient receptor potential cation channel subfamily V member (such as TRPV1 or TRPV4). The TRPV channel changes its state from closed to open by warming up by about 5-10° C. Thus, the change in magnitude B of the magnetic field supplied to the sample 915 should be large enough to increase the temperature of the magnetocaloric actuator 1035 by enough of an amount such that the temperature of the TRPV increases by about 5° C.

As another example, the ion channel 1030 is a transient receptor potential cation channel subfamily M member (such as TRPM8). By contrast, the TRPM channel changes its state from closed to open by cooling down by about 5-10° C. Thus, the change in magnitude B of the magnetic field supplied to the sample 915 should be large enough to decrease the temperature of the magnetocaloric actuator 1035 by enough of an amount so that the temperature of the TRPM decreases by about 5° C.

Referring also to FIG. 9, in some implementations, an increase in the magnitude B of the magnetic field supplied with the DC energy supply 925 causes an increase in the temperature of the magnetocaloric actuator 935 and an increase in the temperature of the thermally-sensitive biological construct 930. And, a decrease in the magnitude B of the magnetic field supplied with the DC energy supply 925 causes a decrease in the temperature of the magnetocaloric actuator 935 and a decrease in the temperature of the thermally-sensitive biological construct 930. For example, a magnetocaloric actuator 1035 in which its magnetically manipulatable material 936i includes gadolinium exhibits this property. For example, the temperature of gadolinium (as the magnetically manipulatable material 936i) increases by about 2.5-3.0° C. for every 1 T increase in the magnitude B of the magnetic field at a physiological or biological temperature.

In other implementations, an increase in the magnitude B of the magnetic field supplied with the DC energy supply 925 causes a decrease in the temperature of the magnetocaloric actuator 935 and a decrease in the temperature of the thermally-sensitive biological construct 930. Moreover, a decrease in the magnitude B of the magnetic field supplied with the DC energy supply 925 causes an increase in the temperature of the magnetocaloric actuator 935 and an increase in the temperature of the thermally-sensitive biological construct 930. A magnetocaloric actuator 935 in which its magnetically manipulatable material 936i includes an alloy of iron-rhodium (FeRh) exhibits this property. For example, the temperature of FeRh (as the magnetically manipulatable material 936i) decreases by about 6.5° C. for every 1 T increase in the magnitude B of the magnetic field at a physiological or biological temperature.

Thus, in this way, the apparatus 900 can be used to either heat or cool the actuator 935, and because of this flexibility, there are more options for how to affect the thermally-sensitive biological construct 930.

Figure 11:
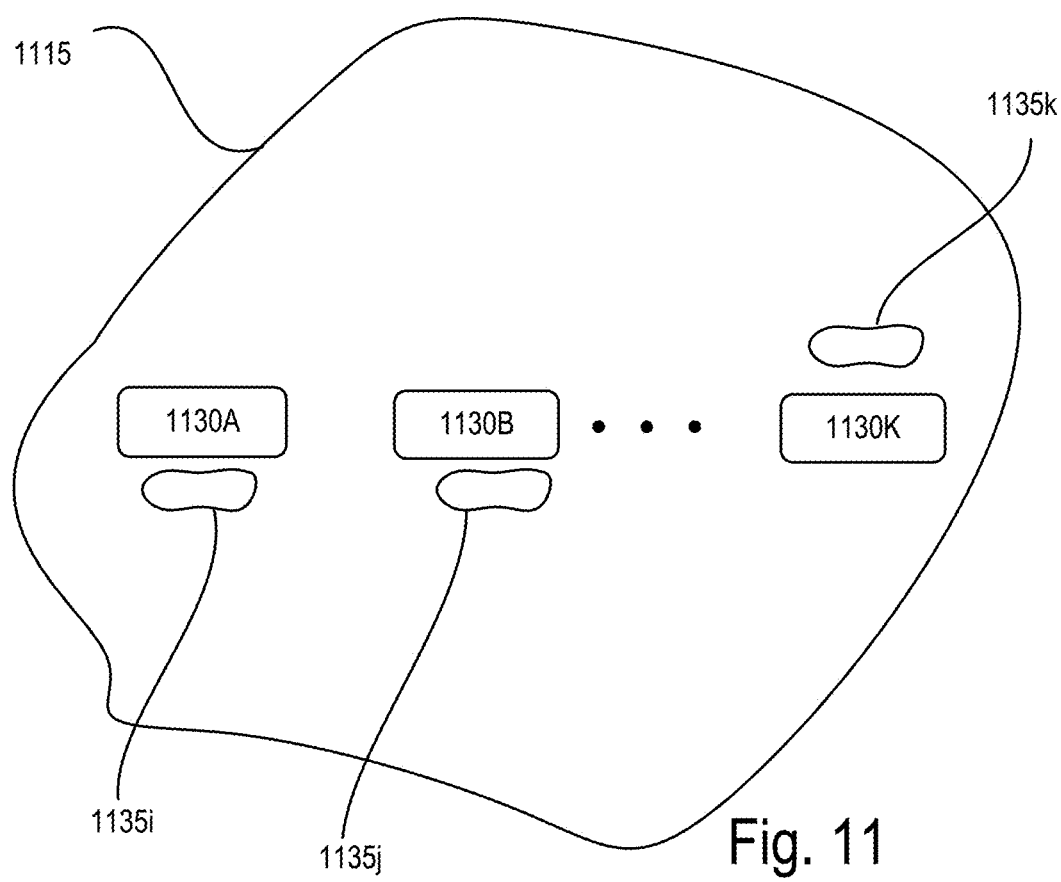
FIG. 11 is a schematic illustration of an implementation of a sample that includes a plurality of thermally-sensitive biological constructs and a magnetocaloric actuator associated with each of these biological constructs.

FIG. 11 is a block diagram of a sample 1115 that includes a plurality of thermally-sensitive biological constructs 1130A, 1130B, . . . 1130K (where K is an integer greater than 2). In some implementations, these biological constructs 1130A, 1130B, . . . 1130K can be associated with the same structure within the sample 1115. In other implementations, one or more of these biological constructs 1130A, 1130B, . . . 1130K are associated with a structure that is different from the structures associated with the other biological constructs. Moreover, a magnetocaloric actuator 1135 can be associated with each of these biological constructs. For example, a magnetocaloric actuator 1135i is thermally coupled with a first thermally-sensitive biological construct 1130A, a magnetocaloric actuator 1135j is thermally coupled with a second thermally-sensitive biological construct 1130B, . . . and a magnetocaloric actuator 1135k is thermally coupled with a last thermally-sensitive biological constructs 1130K. Each magnetocaloric actuator 1135i, 1135j, . . . 1135k is distinct from each of the other magnetocaloric actuators.

Figure 12:
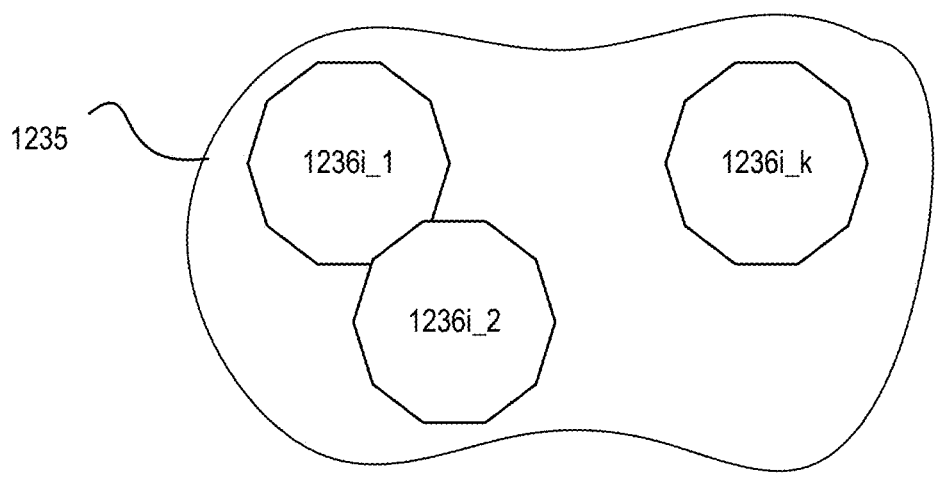
FIG. 12 is a schematic illustration of an implementation of a single magnetocaloric actuator having different magnetically manipulatable materials that are mixed together (but do not interact with each other)

FIG. 12 is a block diagram of a single magnetocaloric actuator 1235 having different magnetically manipulatable materials 1236i, 1236j, 1236k that are mixed together (but do not interact with each other). The labels i, j, and k denote three different types of materials. While only three are shown there can be any number of different materials in the magnetocaloric actuator 1235. For example, the material 1236i can heat up as the magnetic field is decreased while the material 1236j can cool down as the magnetic field is decreased.

Referring again to FIG. 9, the apparatus 900 works with a change in magnetic field that is caused by a DC current from the DC energy supply 925, and thus a thermal magnetic treatment in a biological or medical sample 915 is enabled without the use of AC or RF (radio frequency) fields, which can cause more damage to the sample 915. In Tesla-scale magnetic fields (such as those used in modern magnetic resonance imaging or NMR spectrometers), temperature differences obtained by the magnetocaloric actuator 935 can be on the order of 10° C. or more. Furthermore, in the implementations of FIGS. 10A and 10B, in which the thermally-sensitive biological construct 1030 is an ion channel 1030 positioned along a cellular structure 1017 of the sample 915, these ion channels 1030 can be inserted into biological cells such as neurons, that are sensitive to heat and cold. Temperature differences on the order of 5-10° C. are large enough to open or close such ion channels 1030. Therefore, magnetically manipulatable materials 936i can be on the order of a micron in size (for example 10 μm in diameter), and placed next to such cells, which can be activated by exposing them to magnetic fields that change due to changes supplied by a DC energy supply 925. In this way, the ion channel 1030 can be remotely activated, which means that an invasive procedure that disrupts the sample 915 is not needed in order to activate the ion channel 1030.

Referring to FIG. 13, a test apparatus 1300 is shown for demonstrating the feasibility of using magnetocaloric materials as thermal actuators of temperature-sensitive biological constructs in genetically-modified cells while in a DC magnetic field. FIG. 13 shows a schematic representation of the test apparatus 1300 in which the at least one thermally-sensitive biological construct 930 within the sample 915 is an ion channel (such as discussed above) 1330 positioned in a cellular structure 1317 of a neuron 1318 within a biological sample 1315. The behavior of the neurons 1318 in the sample 1315 is tested with conductors 1319, through which current flows to a current measurement device 1336, and the current value is an indicator of whether the neurons fire in response to some stimulus.

In this test, some of the neurons 1318B are configured with ion channels 1330 while some of the neurons 1318A lack any ion channels 1330. Moreover, some of the neurons 1318A that lack ion channels are thermally coupled with at least one magnetocaloric actuator 1335 while the others of the neurons 1318A that lack ion channels are not thermally coupled with a magnetocaloric actuator 1335. Similarly, some of the neurons 1318B with the ion channels 1330 are thermally coupled with at least one magnetocaloric actuator 1335 while the others of the neurons 1318B with the ion channels 1330 are not thermally coupled with a magnetocaloric actuator 1335. The test apparatus 1300 includes at least one conductor 1319 associated with each neuron 1318. Thus, the conductor 1319 registers a change in current when the neuron 1318 fires. Moreover, the test apparatus 1300 can be configured so that a neuron 1318B only fires when it is activated by the opening or closing of its ion channel 1330. In this way, the effect of the ion channel 1330 changing its state (between open and close) can be measured or detected with the current signal measured from the conductor 1319.

To test, the sample 1315 is placed in an actuation volume (such as volume 910) and a magnetic field having a magnitude B is applied by the magnet (such as magnet 920). The magnitude B of the magnetic field is changed (for example, by changing the DC current from the DC energy supply 925). The change of the magnitude B of the magnetic field causes the temperature of the magnetocaloric actuator 1335 to change, and this temperature change causes a change in status of the ion channel 1330 that is thermally coupled to a magnetocaloric actuator 1335, and this change in status of the ion channel 1330 causes the neuron 1318B to which it is associated or in proximity of to fire (or change its current output). Thus, it is expected that the change in magnitude B of the magnetic field leads to only a change in current output of the neurons 1318B that are associated with ion channels 1330 that are in thermal coupling with an actuator 1335, while the neurons 1318B having ion channels 1330 that are not in thermal coupling with an actuator 1335 and the neurons 1318A should not produce any change in current output.

Switchable and tunable labels with high contrast ratio are developed for MM using magnetocaloric materials that have sharp first order magnetic phase transitions at physiological temperatures and typical MRI magnetic fields. Selection of appropriate magnetic materials for tunable labels in typical MRI settings of Tesla-scale DC magnetic fields and physiological temperatures of around 37° C. is hampered by the basic physical properties of most classical magnetic materials such as iron, iron oxides, and the like. Most magnetic materials have Curie temperatures in the hundreds of degrees Celsius, and therefore have a very flat saturation magnetization with respect to temperature at the physiological body temperatures of around 37° C. (310K). Moreover, standard MRI settings place these labels in large DC magnetic fields typically between 1-20 Tesla where all of these materials are magnetically saturated and therefore have constant contrast in the MRI. Therefore, magnetic materials are identified, designed, or engineered that have switchable and tunable properties with high differential contrast ratios in the MRI settings where the DC magnetic fields are very large (on the scale of Teslas) and in-vivo physiological temperatures are around 37° C.

A magnetocaloric material such as iron-rhodium (FeRh) can be prepared by melt mixing, high-temperature annealing, and ice-water quenching. Temperature and magnetic field dependent magnetization measurements of wire-cut FeRh samples can be performed on a vibrating sample magnetometer. Temperature-dependent MRI of FeRh samples can be performed on 4.7 T scanner.

The magnetocaloric material FeRh can be demonstrated to act as a high contrast ratio switchable MM contrast agent due to its sharp first order magnetic phase transition in DC magnetic field of MRI and at the physiologically relevant temperature. A wide range of magnetocaloric materials are available that can be tuned by materials science techniques to optimize their response under MRI-appropriate conditions and be controllably switched in-situ with temperature, magnetic field, or a combination of both.

Examples of the apparatus, materials, and tests performed on these magnetically manipulatable materials 236 or 936$i$ using the apparatus are described next.

Moreover, the development of novel contrast mechanisms and labeling agents for MRI facilitates further the advancements in non-invasive cell imaging, tracking, and readout of physiological conditions in-vivo. More specifically, the extremely sharp first-order magnetic phase transitions these magnetocaloric materials have at typical physiological temperatures and in the presence of the large DC magnetic field values associated with MM machines provide an ideal match to the requirements for the design of novel MRI labels. Furthermore, a wide range of magnetocaloric materials are available that can be engineered and fine-tuned to optimize their response under MRI-appropriate conditions.

One magnetocaloric material that can be used is iron-rhodium, which is discussed next. The iron-rhodium is prepared by mixing the components (Fe and Rh) in an arc melting furnace. Next, the mixed components are subjected to a high-temperature annealing in an Argon gas quartz tube furnace at 1,000° C. for two weeks, and subsequently rapidly quenched in ice-water. This procedure typically results in the ordered (body-centered-cubic CsCl-type crystal structure) binary alloy FeRh with the bulk saturation magnetization of Ms=$1.3 \times 10^6$ A/m in the ferromagnetic state. The prepared FeRh can be cut into mm-scale sample disks and buffed to a shiny metallic surface with an optical fiber polishing paper in order to remove any oxide from the samples. Temperature and field dependent magnetic measurements of the samples can be performed in a 9-Tesla Vibrating Sample Magnetometer (for example, procured from VSM, Quantum Design, Inc.). In order to demonstrate the basic proof-of-concept feasibility of a magnetocaloric material as a tunable and switchable high differential contrast agent at physiological temperatures and typical MM settings, a 4.7 Tesla MM scanner (produced by Bruker Biospin, Inc.) can be used. The available MRI polarizing magnetic field of such a scanner is closest to the value where the sharp first order magnetic phase transition happens near the physiological temperature of 37° C. (310° K).

Two sets of iron-rhodium granules are prepared for testing. The first set is Fe 49%—Rh 51% atomic composition, of 99% nominal purity and is discussed with reference to FIGS. 14A and 15A and the second set is Fe 49%—Rh 51% atomic composition, of 99.9% nominal purity) and is discussed with reference to FIGS. 14B and 15B. The granules of FeRh can be obtained from American Elements Corporation (Model FE-RH-02 for 99% purity or Model FE-RH-03 for 99.9% purity).

Figure 14A:
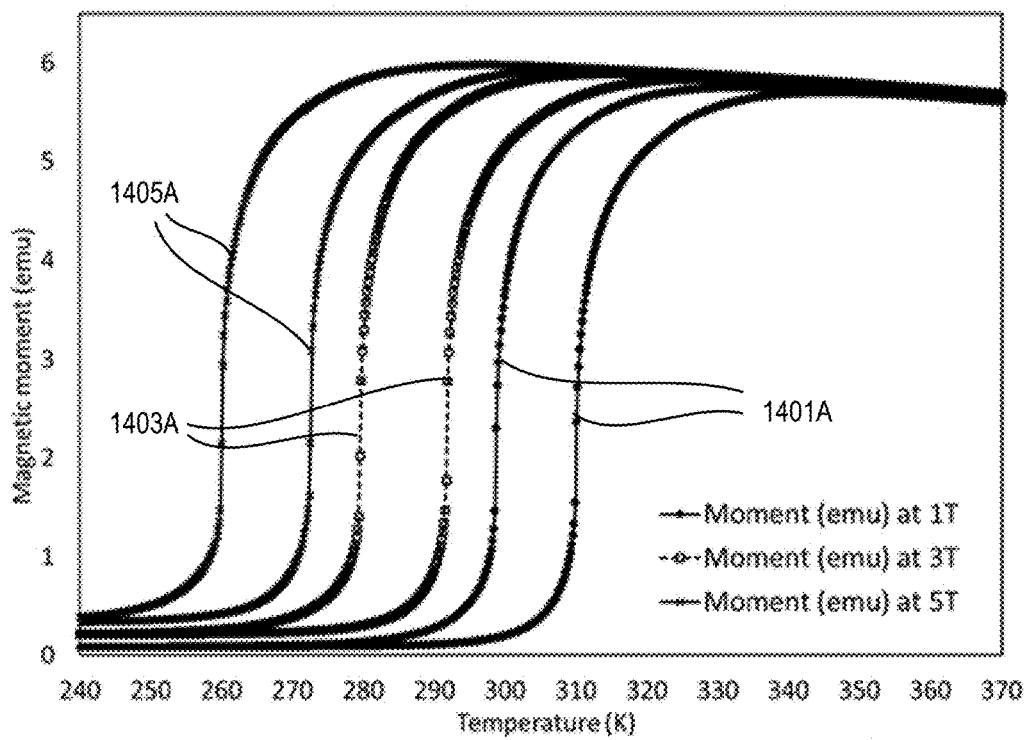
FIG. 14A is a graph of a measurement of the magnetic moment of a 99% purity FeRh structure as a function of temperature in different bias DC magnetic fields.

In FIGS. 14A-15B, the magnetocaloric material (236 or 936$i$) used in the magnetically manipulatable structure is FeRh. FIGS. 14A and 14B show the measurements of the magnetic moment of the FeRh structure as a function of temperature at different constant magnetic fields. Measurements are taken with the 9 T vibrating sample magnetometer. Both FeRh structures exhibited a sharp first order magnetic transition from an antiferromagnetic to a ferromagnetic state over a very narrow range of physiologically relevant temperatures, as discussed next.

FIG. 14A shows the measurement of the magnetic moment of a 99% purity FeRh structure as a function of temperature in different bias DC magnetic fields, for example, 1 T (1401A), 3 T (1403A), and 5 T (1405A). The FeRh structure exhibits a sharp magnetic phase transition from an antiferromagnetic to a ferromagnetic state over a very narrow range of physiologically relevant temperatures. More specifically, the FeRh structure has a sharp transition around body temperature (37° C.=310K) in a constant magnetic field (the DC bias field) of around 1 Tesla.

Figure 14B:
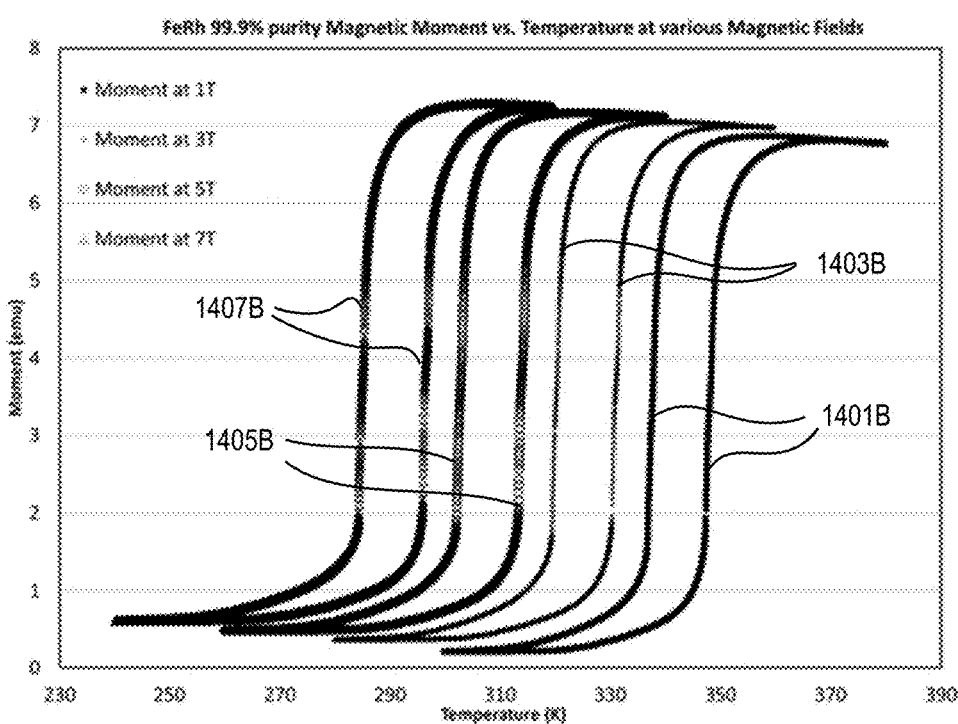
FIG. 14B is a graph of a measurement of the magnetic moment of a 99.9% purity FeRh structure as a function of temperature in different bias DC magnetic fields.

FIG. 14B shows the measurement of the magnetic moment of a 99.9% purity FeRh structure as a function of temperature in different bias DC magnetic fields, for example, 1 T (1401B), 3 T (1403B), 5 T (1405B), and 7 T (1407B). The FeRh structure exhibits a sharp transition from an antiferromagnetic to a ferromagnetic state over a very narrow range of physiologically relevant temperatures. More specifically, the FeRh structure has a sharp magnetic phase transition around body temperature (37° C.=310K) in the DC bias field of around 5 Tesla.

These results are in line with the previously reported measurements of FeRh and demonstrate several features. The most important one is that the magnetization of FeRh changes through the transition by a factor of about 20 in absolute value, and it does so over a very narrow temperature range around the physiological body temperature and in the presence of a large Tesla-scale magnetic field. The second feature is that the temperature dependence and magnetic properties of FeRh (and magneto-caloric materials in general) are highly dependent on the purity of the FeRh. Conversely, this demonstrates the attractive feature of FeRh (and other magneto-caloric materials) that, through careful materials science preparation and process control of impurities and crystal structure, one can tune and engineer FeRh to have a sharp magnetic phase transition at the desired temperature and bias magnetic field (nominally at the physiological body temperature and magnetic field of the MRI machine used). Furthermore, such temperature dependence of magnetization demonstrates that, once the proper magneto-caloric material is prepared for a specific magnetic field of the MRI used, the magnetization of that magneto-caloric label can in principle be switched in-situ by modest temperature changes on the order of a few degrees Celsius.

Figure 15A:
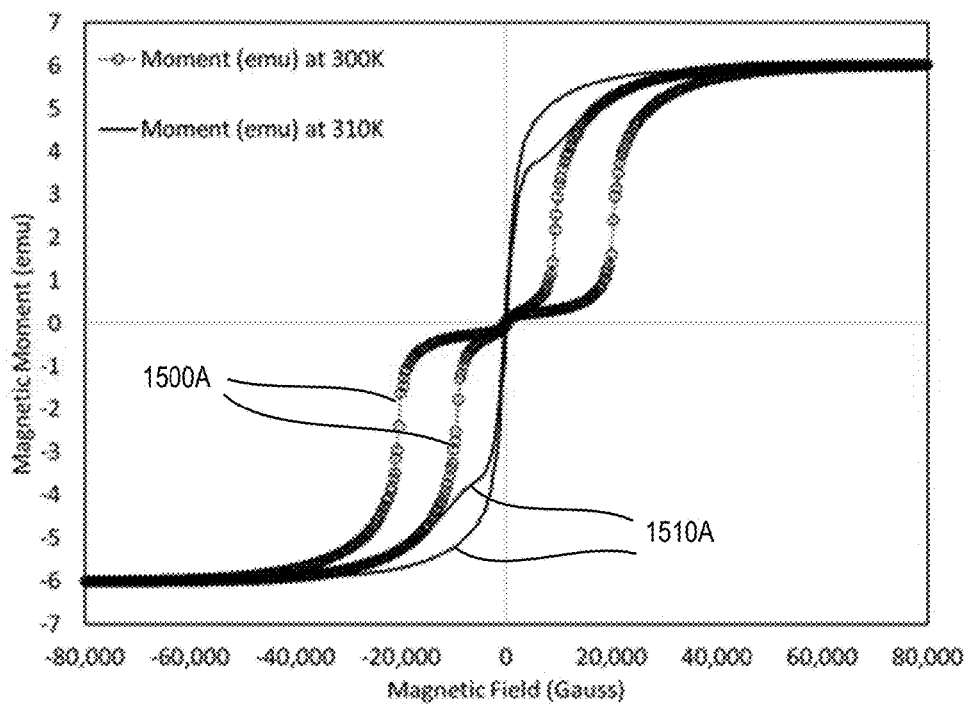
FIG. 15A is a graph of a measurement of the magnetic moment of a 99% purity FeRh structure as a function of varying magnetic field at constant temperature.
Figure 15B:
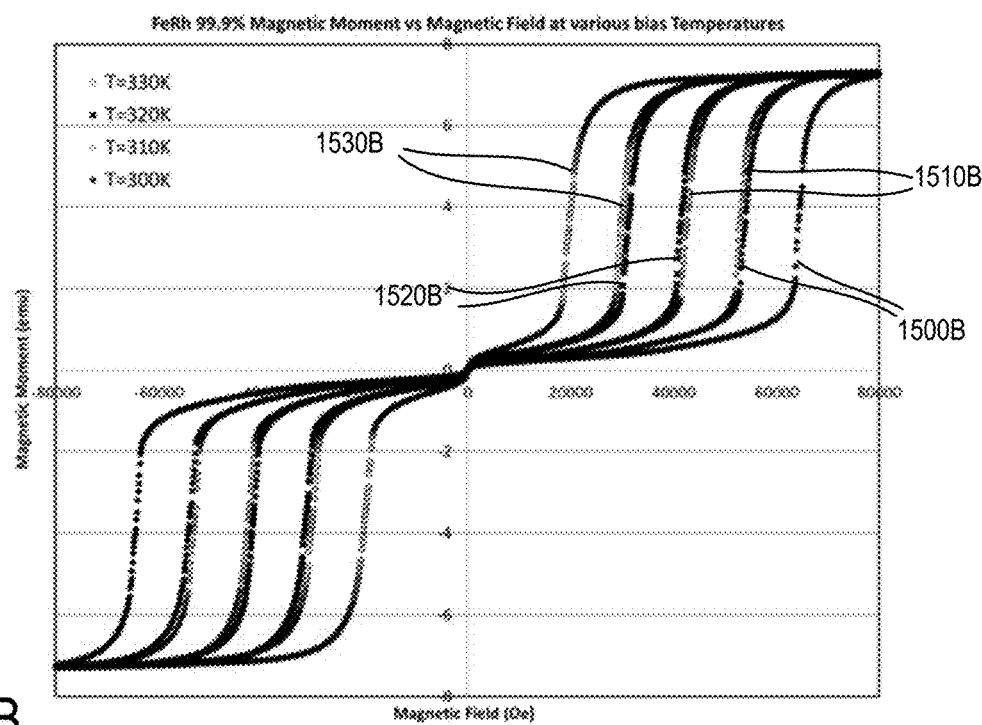
FIG. 15B is a graph of a measurement of the magnetic moment of a 99.9% purity FeRh structure as a function of varying magnetic field at constant temperature.

FIGS. 15A and 15B show the measurements of the magnetic moment of the FeRh structure as a function of varying magnetic field at constant temperature (at a room temperature of 27° C.=300K or at a physiological body temperature of 37° C.=310K, respectively). Measurements are taken with the 9 T vibrating sample magnetometer.

Referring to FIG. 15A, the magnetization of the FeRh structure is tuned with the magnetic field. In this measurement, the magnetic moment of a 99% purity FeRh structure is measured as a function of the magnetic field at various constant temperatures, for example, 310K (1510A) and 300 K (1500A). As evident, the sharp transition is present at large DC magnetic field values and around physiologically relevant temperatures.

Referring to FIG. 15B, the magnetization of the FeRh structure is tuned with the magnetic field. In this measurement, the magnetic moment of a 99.9% purity FeRh structure is measured as a function of the magnetic field at various constant temperatures, for example, 330 K (1530B), 320K (1520B), 310 K (1510B), and 300 K (1500B). Again, the sharp transition is present at large DC magnetic field values and around physiologically relevant temperatures.

Specifically, the 99% purity FeRh structure (FIG. 14A) has a sharp magnetic phase transition around the room and body temperatures at the magnetic field values between 0.5-2 Tesla, while the 99.9% purity FeRh structure (FIG. 14B) has a sharp magnetic phase transition around the room and body temperatures at the magnetic field values between 4-6 Tesla. These results demonstrate another feature that, once the proper magnetocaloric material is fabricated as a switchable MRI label for the specific magnetic field of the MM used, the magnetization of that magnetocaloric label can be switched in-situ with additionally added or subtracted magnetic field or by temporarily removing the sample from the MM bore.

Figure 16:
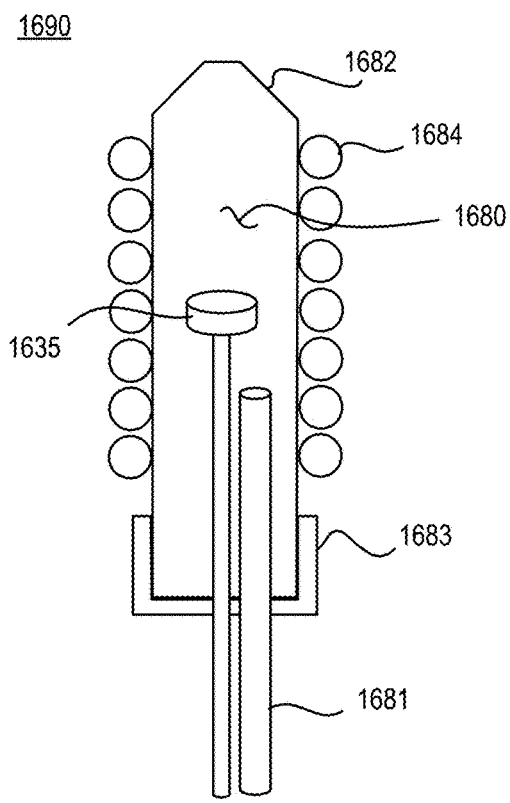
FIG. 16 is a block diagram of an implementation of a testing apparatus to demonstrate operation of the apparatus of FIGS. 1, 2, and 9 in which a disk of FeRh is embedded in agarose next to a thermometer 1681.

Measurements described in FIGS. 14A, 14B, 15A, and 15B guide experimental choices for demonstrating the basic proof-of-concept feasibility of a magnetocaloric FeRh material as a switchable high differential contrast MM agent. Of the two FeRh structures that were prepared, 99.9% purity FeRh structure displayed a sharper first order magnetic transition at a higher bias DC magnetic field (of around 5 Tesla) at the physiological temperature of 37° C. Referring to FIG. 16, for the Mill demonstration, a testing apparatus 1690 is used. In the testing apparatus 1690, the disk of FeRh 1635 is embedded in agarose 1680 next to an MM-compatible optical fiber-based thermometer 1681 (which can be procured from FISO Technologies, Inc.). The disk 1635 and the agarose 1680 are held within a container 1682, which is sealed with a cap 1683. The container 1682 is wrapped in tubing 1684 connected to a temperature-controlled water circulating bath in order to sweep and control the temperature of the disk 1635 and its environment around physiologically relevant temperature range (10-55° C.).

The testing apparatus 1690 of FIG. 16 can be used to create representative gradient-echo images of the effect of the mm-scale disk of FeRh 1635 on the surrounding agarose 1680 as the temperature is swept from the antiferromagnetic phase below the transition temperature to the ferromagnetic phase above the transition temperature of the FeRh structure 1635 and then cooled. In order to produce a gradient-echo image, the testing apparatus 1690 is inserted into a magnet (such as the magnet 120, which in this test case is an MRI magnet). RF pulses and gradient pulses are applied to the entire FeRh structure 1635. The resonant signal from the surrounding agarose 1680 is detected by inductive detection coils of the magnetic apparatus 105 (which is an MRI machine) in which the apparatus 1690 is placed. The resonant signal is affected by how magnetic the FeRh structure 1635 is in the middle of agarose 1680.

Figure 17G:
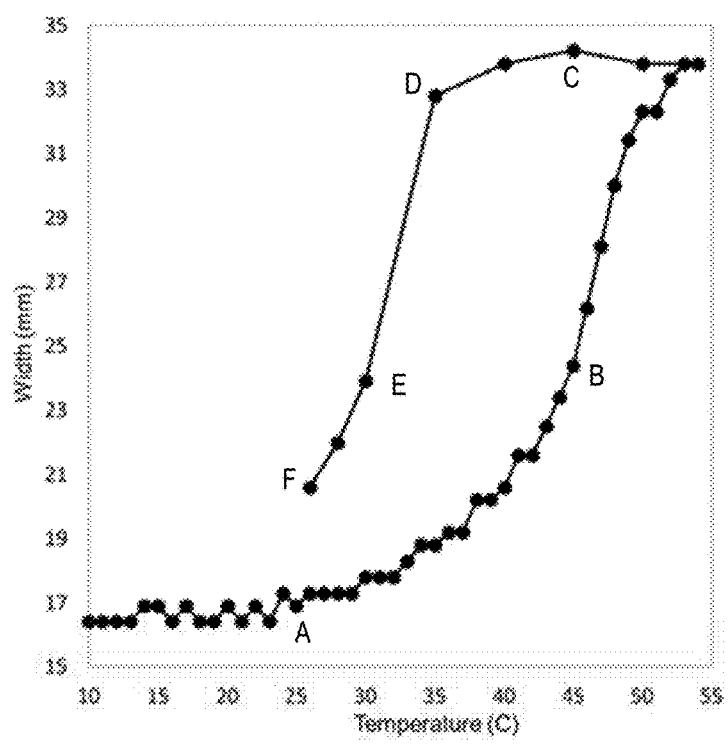
FIG. 17G is a graph of a width of an image artifact (or MRI signal) of FIGS. 17A-17F that is created by signal loss due to the magnetic field gradients from the FeRh disk of FIG. 16 as a function of the set-up temperature.

These gradient-echo images are shown in FIGS. 17A-17F. These images are taken while maintaining the magnetic field magnitude at 4.7 T. The FeRh structure 1635 is 99.9% purity FeRh disk having a volume of 1 mm$^3$. The images are taken through the center of the disk 1635 at various temperatures as the disk 1635 is heated and then cooled. In each of the images, a stable image feature 1781 is visible. This feature 1781 is produced by the thermometer 1681 next to the FeRh disk 1635. The thermometer 1681 is non-magnetic, and thus, it does not exhibit any appreciable change in the images as the magnetic field changes (due to the change in the temperature) from FIG. 17A to FIG. 17F. The feature 1781 is difficult to see in FIGS. 17C and 17D (but it is labeled to show its location) because the signal from the FeRh disk 1635 overwhelms it. FIG. 17G shows a width of the MRI signal 1782 (or image artifact) created by signal loss due to the magnetic field gradients from the FeRh disk 1635 as a function of the set-up temperature.

Figure 17A:
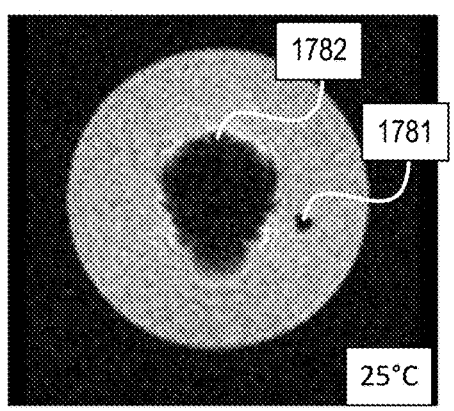
FIGS. 17A-17F are representative gradient-echo images showing the effect of the FeRh mm-scale disk of FIG. 16 on the surrounding agarose as the temperature of the set-up is swept through a physiologically relevant temperature range (10-55° C.) at a constant MM magnetic field of 4.7 Tesla.
Figure 17B:
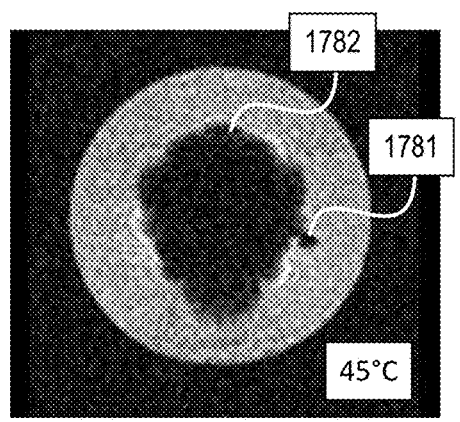
Figure 17C:
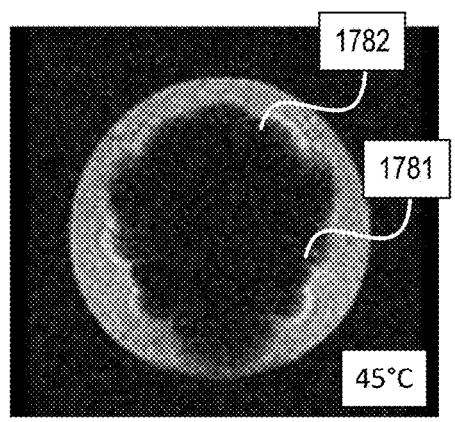
Figure 17D:
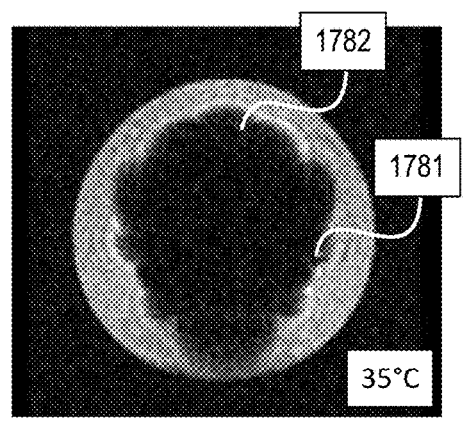
Figure 17E:
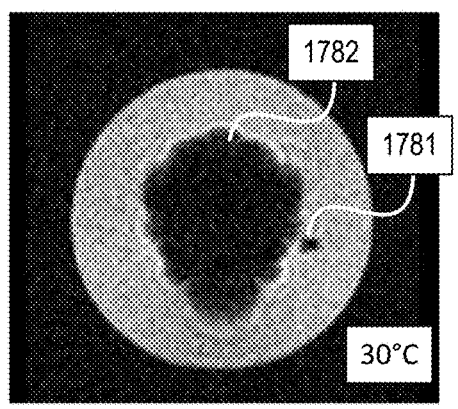
Figure 17F:
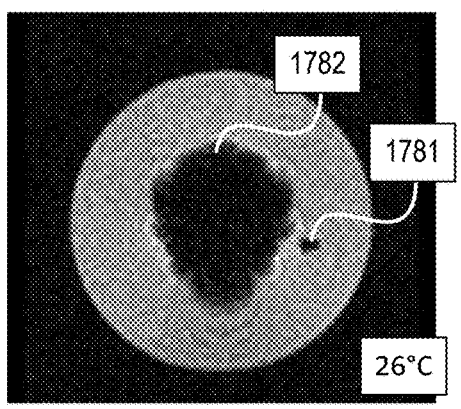

Specifically, FIGS. 17A-17F show six representative gradient-echo images (out of 52) of the effect of the FeRh mm-scale disk 1635 on the surrounding agarose 1680 as the temperature of the set-up is swept through physiologically relevant temperature range (10-55° C.) at the constant MRI magnetic field of 4.7 Tesla. The image parameters are as follows: TR/TE=100/2.2 ms, FA=25 degrees, nominal resolution=0.46×0.46×1 mm, FOV=60.0×60.0 mm. In chronological order, FIG. 17A shows the gradient-echo image taken at a temperature of 25° C.; FIG. 17B shows the gradient-echo image taken at a temperature of 45° C.; FIG. 17C shows the gradient-echo image taken at a temperature of 45° C.; FIG. 17D shows the gradient-echo image taken at a temperature of 35° C.; FIG. 17E shows the gradient-echo image taken at a temperature of 30° C.; and FIG. 17F shows the gradient-echo image taken at a temperature of 26° C.

The demonstrated agarose image phase shift with concomitant magnetic field change emanating from the magnetocaloric FeRh disk 1635 is seen in the increase of the MM signal 1782 around the sample in FIGS. 17A-17F. As the magnetization data of FIG. 14B dictates, the temperature increase drives the FeRh disk 1635 to transition from the low-moment antiferromagnetic phase below the transition temperature to the high-moment ferromagnetic phase above the transition temperature and then back to the low-moment antiferromagnetic phase as the FeRh disk 1635 is cooled. When the magnetically manipulatable material 1635 goes to a magnetic state (for example, increasing temperature for FeRh) from a non-magnetic state, the surrounding substance (for example, agarose 1680), that is, the substance around the magnetically manipulatable material 1635, sees both the background magnetic field produced by the magnet 920 and the magnetic field produced from the now-magnetic material (in this example, the FeRh in the disk 1635). That extra field from the FeRh disk 1635 is non-uniform and in essence alters the Mill signal 1782 around the FeRh to some distance, it puts it out of detection range. This is why the gradient-echo image looks much larger and darker as the magnetic field increases. It is not that the FeRh disk 1635 is any bigger, it is that the FeRh disk 1635 changes its magnetic state, which in turn changes the Mill signal of the surrounding substance 1680 and makes the image change to a larger darker spot.

Loss of signal in the MM of FIGS. 17A-17F due to the changing magnetic state of the magnetocaloric material closely follows the magnetic properties that are shown in FIG. 14B. The size of the region with signal dropout due to the high magnetic field gradients approximately doubles in each dimension, a factor of 8 in volume. This effect is plotted in FIG. 17G, which shows the MM signal loss region size (in a linear dimension) as a function of temperature. The image parameters are as follows: TR/TE=100/2.2 ms, FA=25 degrees, nominal resolution=0.46×0.46×1 mm, FOV=60.0× 60.0 mm.

The clearly demonstrated phase shift with concomitant magnetic field change is seen in the increase of the MRI signal void. There was a larger hysteresis and lower apparent moment increase in the MM data than in the magnetometer data, which may be related to mechanical stress when cutting the material (the FeRh disk 1635) to a smaller size. This hysteresis effect could be viewed as a benefit, in that once a particle in the FeRh disk 1635 is turned "on" then it will remain on until removed from the field.

In general, this result can be assumed to apply for the magnetocaloric materials in the structure 135 when it is placed in the magnet 120. When the magnetocaloric material is in a non-magnetic state (for example, at a low temperature for FeRh or at a high temperature for La—Fe—Si), the water surrounding the structure 135 experiences just the MRI magnetic field supplied by the magnet 120 on the order of Tesla (depending on the scanner magnetic field). But when the magnetocaloric material goes to a magnetic state (for example, at a high temperature for FeRh or at a low temperature for La—Fe—Si), the water around the structure 135 experiences both the MRI scanner magnetic field (from the magnet 120) and the magnetic field from the now magnetic magnetocaloric material in the structure 135. That extra field from the magnetic magnetocaloric material is non-uniform and in essence alters the MM water signal around the structure 135 to some distance, it puts it out of detection range.

Figure 18A:
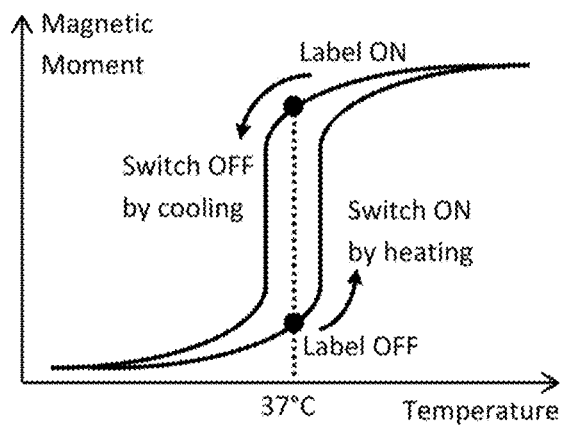
FIG. 18A is a graph of a magnetic moment of a magnetocaloric material versus temperature, which shows a transition from a first magnetic state to a second magnetic state, in which the center of the first order magnetic phase transition of the magnetocaloric material is at the physiological temperature of 37° C.
Figure 18B:
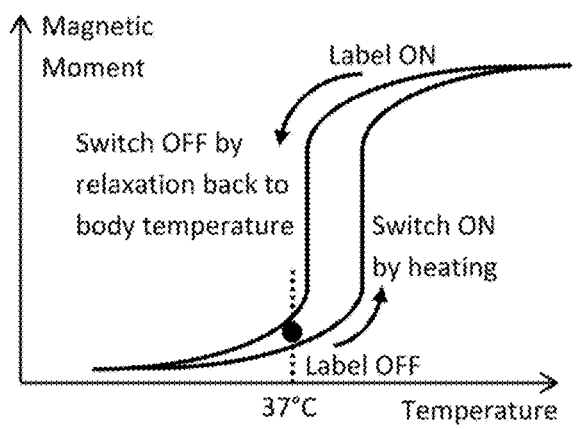
FIG. 18B is a graph of a magnetic moment of a magnetocaloric material versus temperature, which shows a transition from a first magnetic state to a second magnetic state, in which the center of the first order magnetic phase transition of the magnetocaloric material is greater than the physiological temperature of 37° C.
Figure 18C:
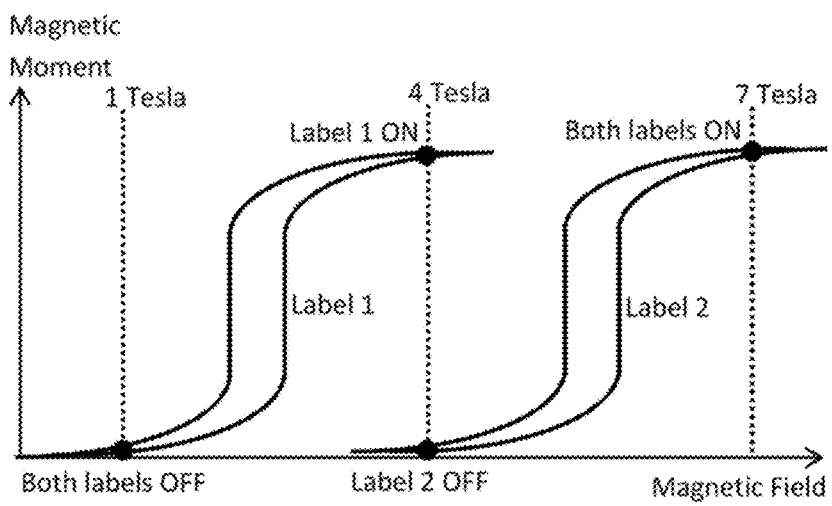
FIG. 18C is a graph of a magnetic moment of two magnetocaloric materials that have phase transitions at two different magnetic field values at the physiological temperature.

Switching protocols for using FeRh as the magnetically manipulatable structure 135 are discussed next with reference to FIGS. 18A-18C. A switching protocol describes the transition of the magnetocaloric material in the structure 135 from the first magnetic state to the second magnetic state. FIG. 18A shows the MRI magnetic field at the value where the center of the first order magnetic phase transition of the magnetocaloric material is at the physiological temperature of 37° C. Temporary heating and cooling switches the magnetocaloric material between the MRI visible (ON) and invisible (OFF) states. FIG. 18B shows the MRI magnetic field is at the value where the center temperature of the magnetocaloric material first order magnetic phase transition is higher than the physiological temperature of 37° C. Temporary heating switches the magnetocaloric material to the MM visible (ON) state while thermal relaxation to equilibrium temperature brings the magnetocaloric material back to the MM invisible (OFF) state. FIG. 18C shows the multiplexing of two magnetocaloric materials that have phase transitions at two different magnetic field values at the physiological temperature. The two magnetocaloric materials are visible or invisible at different magnetic fields and can therefore be differentiated in images from different MRI scanners (in this example at 1 T, 4 T, and 7 T).

As discussed above, FeRh is a suitable switchable and tunable magnetocaloric material in the typical MM settings (Tesla-scale magnetic fields) and in-vivo physiological temperatures (around 37° C.) through a very sharp first order magnetic phase transition. FeRh is only one in a large repertoire of magnetocaloric materials that have similar switching characteristics under similar environmental conditions, where sharp first order magnetic phase transition with a positive M vs. T slope is observed at physiological temperatures and Tesla-scale magnetic fields. Furthermore, there are many magnetocaloric materials where the sharp first-order magnetic phase transitions can also have a negative M vs. T slope at physiological temperatures and Tesla-scale fields, or even a combination of sharp positive and negative slopes, making magnetocaloric compounds even stronger candidates as versatile materials for high differential contrast switchable MM labels.

The switching protocols can be used for in-vivo MM settings. The Mill contrast agent using FeRh can be reversibly switched by thermal cycling of the entire sample set-up over the physiologically relevant temperature range. Other potential engineering solutions to magnetocaloric Mill label switching include heating by Mill compatible focused ultrasound or high-frequency inductive heating, cooling by Mill compatible thermo-electric coolers, or magnetocaloric material switching by adding or subtracting to the main magnetic field of the Mill (in the simplest version this can be accomplished by temporarily removing the sample from the Mill bore).

When considering such Mill label switching solutions, magneto-thermal properties of the magnetocaloric material are also considered, especially the location of the first order magnetic phase transition of the magnetocaloric material. FIGS. 18A-18C schematically describe specific examples. In FIG. 18A, the MM label has two stable magnetic states (indicated by the solid black dots) at 37° C. (310K). This example is well represented by the 99.9% purity FeRh magnetocaloric material at 5 Tesla, as shown in FIG. 14B. In the low magnetic moment state the magnetocaloric material is Mill invisible (Label OFF). The magnetocaloric material can be switched on by temporarily raising its temperature by few degrees C. (approximately ΔT=5° C. for our 99.9% purity FeRh magnetocaloric material at 5 Tesla shown in FIG. 14B) through application of a heating pulse (by any of the above listed potential methods). Once the magnetocaloric material is thermally relaxed back to the equilibrium temperature of 37° C., it remains in the high magnetic moment state and is MIll visible (Label ON). It can be switched off again by active cooling where the temperature of the magnetocaloric material is temporarily lowered. Once the magnetocaloric material relaxes back to the equilibrium temperature of 37° C., it will be in the low magnetic moment state and again MRI invisible (Label OFF). This is also the procedure performed for obtaining the gradient-echo images as described in FIGS. 17A-17F.

The second possibility is described in FIG. 18B. In this case the magnetocaloric material has only one stable magnetic state (indicated by the solid black dot) at 37° C. (310K). This example is well represented by 99.9% purity FeRh magnetocaloric material at 3 Tesla, as shown in FIG. 14B. In this low magnetic moment state the magnetocaloric material is MRI invisible (Label OFF). The magnetocaloric material can be temporarily switched on by raising its temperature through application of a larger heat pulse than was described in FIG. 18A since higher temperature change is required to take the magnetocaloric material through the first order magnetic phase transition (In the case of our 99.9% purity FeRh at 3 T as shown in FIG. 14B, it would take approximately ΔT=20° C. to switch the magnetocaloric material). The magnetocaloric material remains MRI visible (Label ON) in the high magnetic moment state as long as the temperature of the magnetocaloric material is above the phase transition temperature. As the magnetocaloric material thermally relaxes back to the equilibrium temperature of 37° C., it automatically goes back through the phase transition into a low magnetic moment state and becomes MM invisible again (Label OFF). The advantage of this configuration is that active cooling is not required for switching the magnetocaloric material into the MM invisible OFF state, while the disadvantage is that the higher temperature increase is required to temporarily switch the label into the MM visible ON state.

Another feature of MRI switchable labels brought about by the variety of magneto-thermal properties of magnetocaloric materials is the possibility of multiplexed labels made MRI visible or invisible at different magnetic field or temperature values by appropriate materials science design. FIG. 18C describes the possibility of two switchable MRI labels that can be differentiated in images from MRI scanners operating at different magnetic field values. Label 1 has a first order magnetic phase transition at 2 Tesla and is well represented by the 99% purity FeRh magnetocaloric material at 27° C. (300K) shown in FIG. 15A. Label 2 has a first order magnetic phase transition at 6 Tesla and is well represented by the 99.9% purity FeRh magnetocaloric material at 27° C. (300K) shown in FIG. 15B. In a 1 T MRI scanner, both of these labels would be in the low magnetic moment state below their respective first order magnetic phase transition temperatures and therefore invisible in the MM (both labels OFF). In a 4 T MRI scanner, Label 1 would be in the high magnetic moment state above its magnetic phase transition temperature and therefore MM visible (Label 1 ON), while Label 2 would still be in the low magnetic moment state below its magnetic phase transition temperature and therefore still MRI invisible (Label 2 OFF). Finally, in a 7 T MM scanner, both of these labels would be in the high magnetic moment states above their respective magnetic phase transition temperatures and therefore MM visible (both labels ON). Images from these MM scanners with different operating DC magnetic fields would readily differentiate the two labels.

Figure 19A:
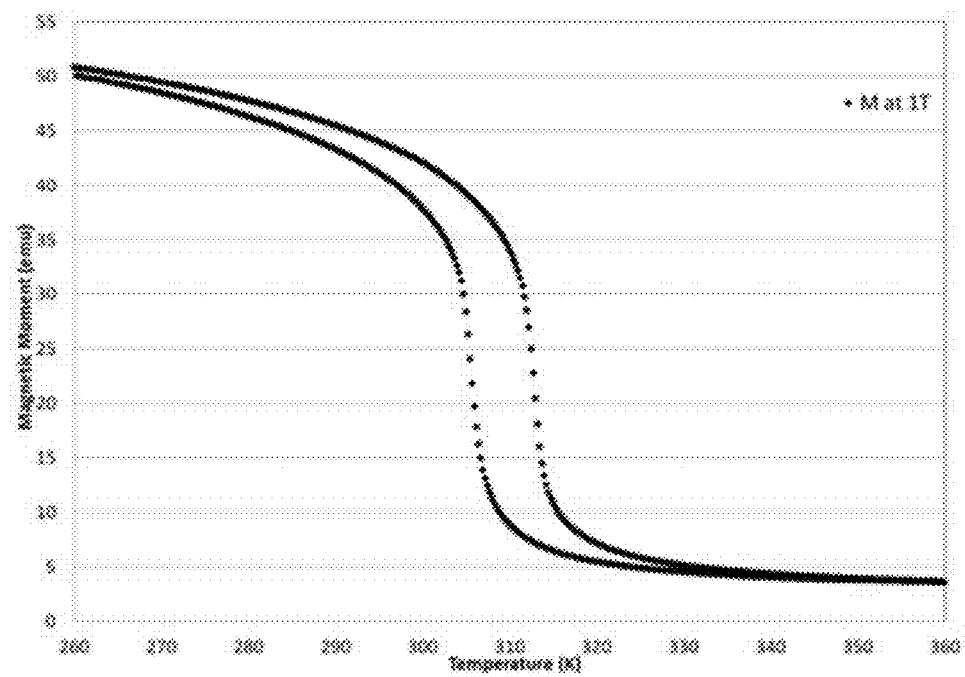
FIG. 19A is a graph of a magnetic moment of first magnetically manipulatable material versus temperature, in which the magnetically manipulatable material is Fe—La—Si.
Figure 19B:
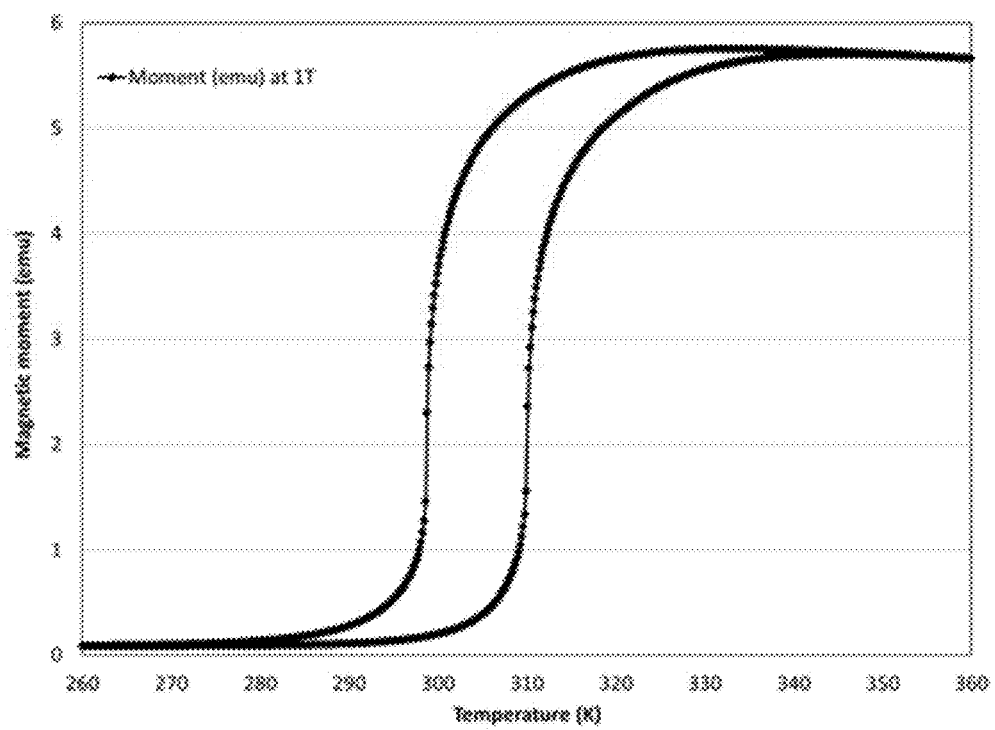
FIG. 19B is a graph of a magnetic moment of first magnetically manipulatable material versus temperature, in which the magnetically manipulatable material is 99% purity FeRh.

Referring to FIGS. 19A and 19B, two different magnetically manipulatable materials are shown that function similarly to the examples shown in FIGS. 6A and 6B, respectively. In FIG. 19A, the magnetically manipulatable material is Fe—La—Si, while in FIG. 19B, the magnetically manipulatable material is 99% purity FeRh. FIG. 19A is a graph of the magnetic state of Fe—La—Si versus temperature T within the sample 115, while maintaining the sample 115 at a constant magnetic field of 1 T. As shown in this graph, Fe—La—Si transitions from a magnetic to a non-magnetic state with a rise in the temperature T. FIG. 19B is a graph of the magnetic state of 99% purity FeRh versus temperature T within the sample 115, while maintaining the sample 115 at a constant magnetic field of 1 T. As shown in this graph, FeRh transitions from a non-magnetic to a magnetic state with a rise in the temperature T.

Figure 20:
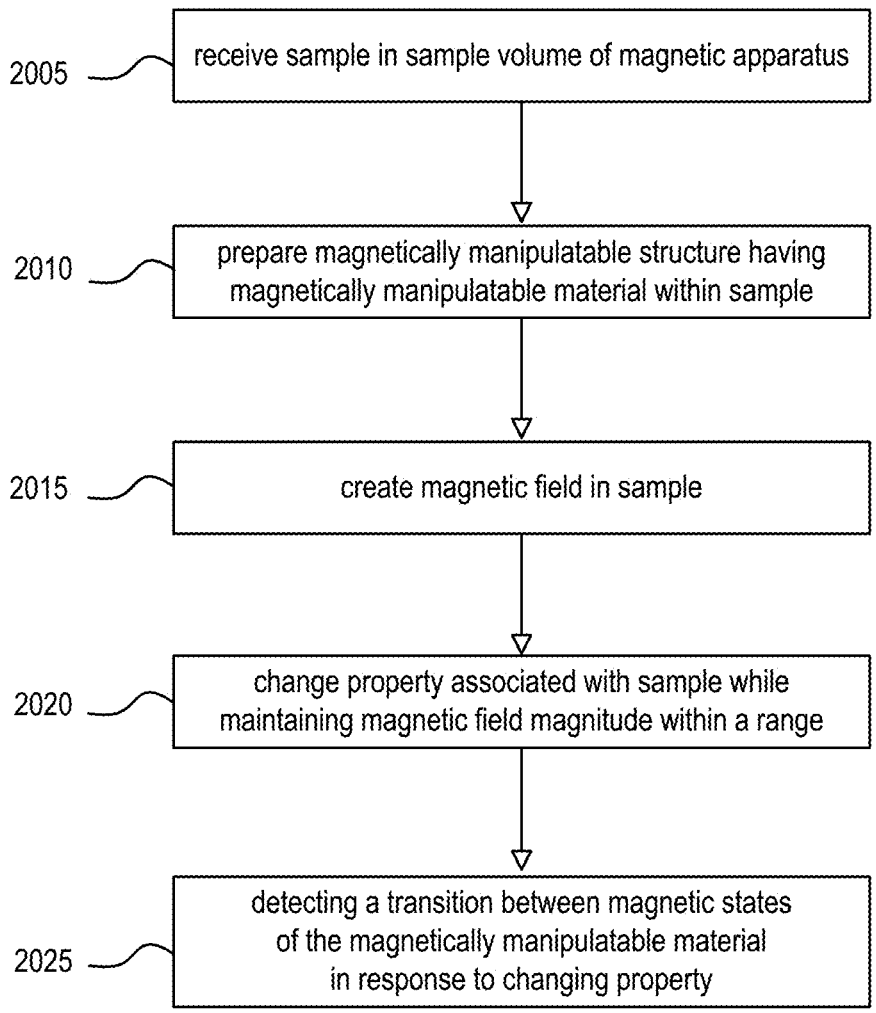
FIG. 20 is a flow chart of a procedure performed by the apparatus of FIG. 2 for using the magnetic apparatus and the magnetically manipulatable structure to control, alter, or operate on the sample.

Referring to FIG. 20, a procedure 2000 is performed by the apparatus 200 for using the magnetic apparatus 205 and the magnetically manipulatable structure 235 to control, alter, or operate on the sample 215. For example, the structure 235 can include the magnetically manipulatable materials 236, the magnetic apparatus 205 can be an MM machine, and the materials 236 can act as one or more tunable and switchable labels in the MRI machine 205.

The procedure 2000 includes receiving the sample 215 in the sample volume 210 defined by the magnetic apparatus 205 and the magnet 220 (2005). The sample 215 can be placed inside the magnet 220 using any suitable technique that is used in MRI machines. The sample 215 can be a whole living organism, or it can be a portion or a region of a living organism. The magnetically manipulatable structure 235 and the material 236 are prepared within the sample 215 (2010). For example, the structure 235 can be embedded within the sample 215 using the injection apparatus 260 and this can occur prior to or after the sample 215 is placed inside the magnet 220.

The magnetic field having the magnitude B is created in the sample 215 (2015). For example, the control system 240 can send a signal to the energy supply 225 to provide current to the electrically conductive wire coils of the magnet 220. The magnitude B of the magnetic field is generally greater than 0.5 Tesla and can be in a range of 1-20 Tesla.

A property associated with the sample 215 is changed while generally maintaining the magnetic field magnitude B constant in the sample 215 (2020). The property that is changed (2020) can be the magnetic field or a temperature or both the magnetic field and the temperature of the sample 215. If the property that is changed is the magnetic field, then the change in the magnetic field is substantially smaller than the magnitude B of the field that is held constant. The change in magnetic field is at least an order of magnitude smaller than the magnitude B. Similarly, if the overall temperature of the sample 215 is between about 270-370 K, and the property to be changed (2020) is the temperature, then the change in the temperature is substantially less than the overall temperature of the sample 215. For example, the temperature change can be about 10-40 K. The change in the property (2020) can be affected by the sample property scanning system 245, as discussed above.

Because the magnetically manipulatable structure 235 includes magnetically manipulatable materials 236, the change in the property (2020) causes the magnetically manipulatable materials 236 to transition from a first magnetic state to a second magnetic state, and this transition causes a change in the sample 215 near to the structure 235. This change in the sample 215 is detected (2025). This means that the structure 235 can be turned on and off by the procedure 2000 and has the effect that it can be used as a high-contrast tunable and switchable label for MRI machines 205. The structure 235 can therefore be used as an MRI contrast agent or a sensor because of these properties. Thus, the change in the magnetization of the magnetically manipulatable materials 236 of the structure 235 can be detected by the apparatus 200 by observing the effect the change has on the water or biological tissue surrounding the materials 236.

Figure 21:
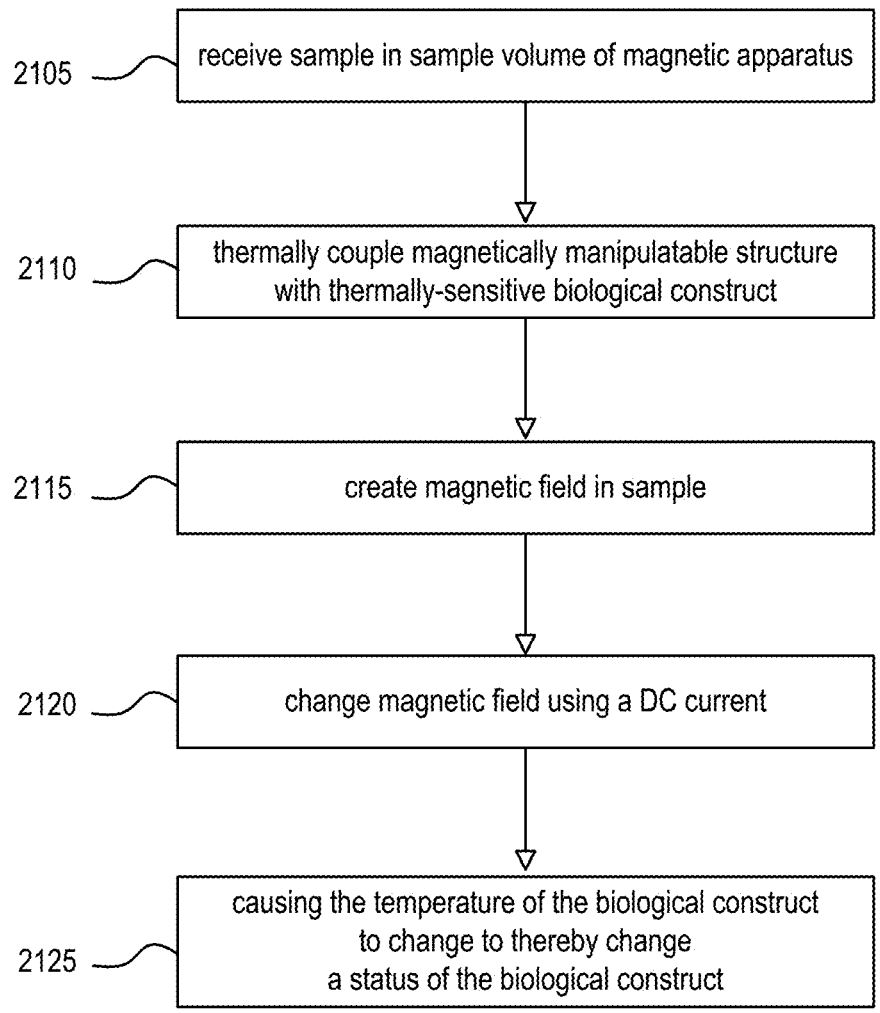
FIG. 21 is a flow chart of a procedure performed by the apparatus of FIG. 9 for actuating (for example, activating and de-activating) a biological construct (which can be the thermally-sensitive biological construct within the sample.

Referring to FIG. 21, a procedure 2100 is performed by the apparatus 900 for actuating (for example, activating and de-activating) a biological construct (which can be the thermally-sensitive biological construct 930) within a sample 915. The sample 915 is received in the actuation volume 910 defined by the magnet 920 of the magnetic apparatus 905 (2105). The magnetically manipulatable structure 935 is physically (for example, thermally) coupled with the biological construct within the sample 915 (2110) such that the biological construct changes its status in response to a change in property of the magnetically manipulatable structure 935. Thus, if the physical coupling is a thermal coupling and the biological construct is a thermally-sensitive biological construct 930, then the thermally-sensitive biological construct 930 changes its status in response to a change in a temperature of the magnetically manipulatable structure 935.

The magnetic field having the magnitude B is created in the sample 915 (2115). For example, the control system 940 can send a signal to the energy supply 925 to provide current to the electrically conductive wire coils of the magnet 920. The magnitude B of the magnetic field is generally greater than 0.5 Tesla and can be in a range of 1-20 Tesla.

A characteristic within the sample 915 is changed (2120) For example, the characteristic of the sample 915 that is changed (2120) is the magnetic field within the sample, 915. The magnetic field within the sample 915 can be changed by changing a DC current supplied to the magnet 920. The change in the magnetic field is substantially smaller than the magnitude B of the field that is held constant. The change in magnetic field is at least an order of magnitude smaller than the magnitude B. The change in the characteristic within the sample 915 (2120) can be affected by the sample property scanning system 245, as discussed above.

The change in the characteristic (such as the magnetic field) (2120) causes the property (such as the temperature) of the magnetically manipulatable material 936i to change, and this causes a change in a status of the biological construct (2125). The change to the status of the biological construct (2125) can occur without causing a change in the status of other materials within the sample 915. For example, the change in the magnetic field (212) causes a change in the temperature of the magnetically manipulatable material 936i, and this causes a change in the status of the thermally-sensitive biological construct 930.

What is claimed is:

1. A method comprising:
   receiving a sample in a sample volume defined by a magnetic apparatus;
   thermally coupling at least one magnetocaloric actuator within the sample with a thermally-sensitive biological construct within the sample such that the biological construct changes its status in response to a change in a temperature of the magnetocaloric actuator;
   creating, with a DC current supplied to the magnetic apparatus, a magnetic field having a magnitude B in the sample, the magnitude B being greater than 0.5 Tesla (T) and up to 20 T; and
   changing a status of the thermally-sensitive biological construct by:
      changing the magnitude B of the magnetic field in the sample by an amount that is in the range 1-20 T by changing the DC current supplied to the magnetic apparatus, to thereby affect a magnetic phase transition in the magnetocaloric actuator between a first magnetic state and a second magnetic state that is distinct from the first magnetic state,
      wherein the magnetic phase transition in the magnetocaloric material causes the temperature of the magnetocaloric actuator to change, which causes the change in the status of the thermally-sensitive biological construct.

2. The method of claim 1, wherein changing the magnitude B of the magnetic field in the sample comprises changing the magnitude B of the magnetic field by 2 T.

3. The method of claim 1, wherein changing the status of the thermally-sensitive biological construct comprises changing the thermally-sensitive biological construct from a closed state to an open state.

4. The method of claim 1, wherein the temperature change caused to the magnetocaloric actuator occurs without causing a change in status of materials within the sample other than the at least one thermally-sensitive biological construct.

5. The method of claim 1, wherein:
   increasing the magnitude B of the magnetic field causes the temperature of the magnetocaloric actuator to increase and the temperature of the thermally-sensitive biological construct to increase; and
   decreasing the magnitude B of the magnetic field causes the temperature of the magnetocaloric actuator to decrease and the temperature of the thermally-sensitive biological construct to decrease.

6. The method of claim 1, wherein:
   increasing the magnitude B of the magnetic field causes the temperature of the magnetocaloric actuator to decrease and the temperature of the thermally-sensitive biological construct to decrease; and
   decreasing the magnitude B of the magnetic field causes the temperature of the magnetocaloric actuator to increase and the temperature of the thermally-sensitive biological construct to increase.

7. The method of claim 1, wherein the temperature of an environment of the sample is maintained at a value between 270 and 370 K.

8. The method of claim 1, wherein changing the magnitude B of the magnetic field in the sample comprises changing the magnitude B of the magnetic field by an amount that is smaller than the magnitude B.

9. The method of claim 1, wherein the sample is a living organism, the method further comprising maintaining a temperature of the sample at a physiological temperature to maintain the organism in a living state.

10. The method of claim 1, wherein the magnetocaloric actuator includes a material selected from the group consisting of iron-rhodium, alloys of iron-rhodium, alloys of manganese arsenide, Heusler alloys, alloys of manganese-iron, and gadolinium.

11. The method of claim 1, wherein the sample is a living organism, the method further comprising maintaining a sample environment at a physiological temperature to maintain the organism in a living state.

12. The method of claim 1, wherein the thermally-sensitive biological construct includes an ion channel.

13. The method of claim 12, wherein the ion channel is a transient receptor potential cation channel subfamily V member or a transient receptor potential cation channel subfamily M member.

14. The method of claim 1, wherein:
changing the magnitude B of the magnetic field in the sample comprises increasing the magnitude B of the magnetic field associated with the sample, which causes the temperature of the magnetocaloric actuator to increase; and
changing the magnitude B of the magnetic field in the sample comprises decreasing the magnitude B of the magnetic field associated with the sample, which causes the temperature of the magnetocaloric actuator to decrease.

15. The method of claim 1, wherein:
changing the magnitude B of the magnetic field in the sample comprises increasing the magnitude B of the magnetic field associated with the sample, which causes the temperature of the magnetocaloric actuator to decrease; and
changing the magnitude B of the magnetic field in the sample comprises decreasing the magnitude B of the magnetic field associated with the sample, which causes the temperature of the magnetocaloric actuator to increase.

16. The method of claim 1, wherein the change caused to the temperature of the magnetocaloric actuator occurs without causing a change in status of materials within the sample other than the at least one biological construct.

17. The method of claim 1, wherein creating the magnetic field having the magnitude B in the sample comprises supplying energy to a magnet that creates the magnetic field.

18. The method of claim 17, wherein supplying energy to the magnet comprises supplying a constant DC current through electrically conductive wire coils that form the magnet.

19. The method of claim 1, wherein thermally coupling the at least one magnetocaloric actuator within the sample with the thermally-sensitive biological construct within the sample comprises physically coupling the at least one magnetocaloric actuator with an ion channel that has a status that is either closed or open.

20. The method of claim 1, wherein the temperature of the magnetocaloric actuator is changed by increasing the temperature or decreasing the temperature.

21. A method comprising:
receiving a sample in a sample volume defined by a magnetic apparatus;
thermally coupling at least one magnetocaloric actuator within the sample with a thermally-sensitive biological construct within the sample such that the biological construct changes its status in response to a change in a temperature of the magnetocaloric actuator;
creating a magnetic field having a magnitude B in the sample; and
changing a status of the thermally-sensitive biological construct by:
changing the magnitude B of the magnetic field in the sample by an amount in a range of 1 Tesla (T) to 20 T by changing a DC current supplied to the magnetic apparatus, to thereby affect a magnetic phase transition in the magnetocaloric actuator between a first magnetic state and a second magnetic state that is distinct from the first magnetic state,
wherein the magnetic phase transition in the magnetocaloric material causes the temperature of the magnetocaloric actuator to change, which causes the change in the status of the thermally-sensitive biological construct, and
wherein the temperature change in the magnetocaloric actuator is less than 20° C. for a change in magnetic field magnitude of between 1-20 T.

22. The method of claim 21, wherein the change in temperature (dT) of the magnetocaloric actuator is given by:

$$dT = -\frac{T}{C_B} \times \left(\frac{\partial M}{\partial T}\right)_B dB$$

where T is the temperature of the magnetocaloric actuator, $C_B$ is the heat capacity of the magnetocaloric actuator, $\partial M/\partial T$ is the slope of the magnetization of the magnetocaloric actuator versus the temperature T at the magnitude B, and dB is the change in the magnetic field magnitude.

23. The method of claim 22, wherein the change in temperature dT is negative if either but not both of $\partial M/\partial T$ or dB is negative and the change in temperature dT is positive if both $\partial M/\partial T$ and dB are negative or positive.

24. A method comprising:
receiving a sample in a sample volume defined by a magnetic apparatus;
thermally coupling at least one magnetocaloric actuator with a thermally-sensitive biological construct within the sample such that the biological construct changes its status in response to a change in a temperature of the magnetocaloric actuator, wherein the at least one magnetocaloric actuator is 1-100 micrometers (μm) in size;
creating a magnetic field having a magnitude B in the sample; and
changing a status of the thermally-sensitive biological construct by:
changing the magnitude B of the magnetic field in the sample by changing a DC current supplied to the magnetic apparatus, to thereby affect a magnetic phase transition in the magnetocaloric actuator between a first magnetic state and a second magnetic state that is distinct from the first magnetic state,
wherein the magnetic phase transition in the magnetocaloric material causes the temperature of the magnetocaloric actuator to change, which causes the change in the status of the thermally-sensitive biological construct; and
wherein the change in temperature (dT) of the magnetocaloric actuator is given by:

$$dT = -\frac{T}{C_B} \times \left(\frac{\partial M}{\partial T}\right)_B dB$$

in which T is the temperature of the magnetocaloric actuator, $C_B$ is the heat capacity of the magnetocaloric actuator, $\partial M/\partial T$ is the slope of the magnetization of the magnetocaloric actuator versus the temperature T at the magnitude B, and dB is the change in the magnetic field magnitude.

25. The method of claim 21, wherein changing the magnitude B of the magnetic field in the sample comprises changing the magnitude B of the magnetic field by 2 T.

26. The method of claim 21, wherein changing the status of the thermally-sensitive biological construct comprises changing the thermally-sensitive biological construct from a closed state to an open state.

27. The method of claim 21, wherein the at least one magnetocaloric actuator is 1-100 micrometers (μm) in size.

28. The method of claim 21, wherein the temperature change caused to the magnetocaloric actuator occurs without causing a change in status of materials within the sample other than the at least one thermally-sensitive biological construct.

29. The method of claim 21, wherein:
increasing the magnitude B of the magnetic field causes the temperature of the magnetocaloric actuator to increase and the temperature of the thermally-sensitive biological construct to increase; and
decreasing the magnitude B of the magnetic field causes the temperature of the magnetocaloric actuator to decrease and the temperature of the thermally-sensitive biological construct to decrease.

30. The method of claim 21, wherein:
increasing the magnitude B of the magnetic field causes the temperature of the magnetocaloric actuator to decrease and the temperature of the thermally-sensitive biological construct to decrease; and
decreasing the magnitude B of the magnetic field causes the temperature of the magnetocaloric actuator to increase and the temperature of the thermally-sensitive biological construct to increase.

31. The method of claim 21, wherein the temperature of an environment of the sample is maintained at a value between 270 and 370 K.

32. The method of claim 21, wherein the sample is a living organism, the method further comprising maintaining a temperature of the sample at a physiological temperature to maintain the organism in a living state.

33. The method of claim 21, wherein the magnetocaloric actuator includes a material selected from the group consisting of iron-rhodium, alloys of iron-rhodium, alloys of manganese arsenide, Heusler alloys, alloys of manganese-iron, and gadolinium.

34. The method of claim 21, wherein the sample is a living organism, the method further comprising maintaining a sample environment at a physiological temperature to maintain the organism in a living state.

35. The method of claim 21, wherein the thermally-sensitive biological construct includes an ion channel.

36. The method of claim 35, wherein the ion channel is a transient receptor potential cation channel subfamily V member or a transient receptor potential cation channel subfamily M member.

37. The method of claim 21, wherein:
changing the magnitude B of the magnetic field in the sample comprises increasing the magnitude B of the magnetic field associated with the sample, which causes the temperature of the magnetocaloric actuator to increase; and
changing the magnitude B of the magnetic field in the sample comprises decreasing the magnitude B of the magnetic field associated with the sample, which causes the temperature of the magnetocaloric actuator to decrease.

38. The method of claim 21, wherein:
changing the magnitude B of the magnetic field in the sample comprises increasing the magnitude B of the magnetic field associated with the sample, which causes the temperature of the magnetocaloric actuator to decrease; and
changing the magnitude B of the magnetic field in the sample comprises decreasing the magnitude B of the magnetic field associated with the sample, which causes the temperature of the magnetocaloric actuator to increase.

* * * * *